United States Patent [19]

Binder et al.

[11] Patent Number: 5,679,678
[45] Date of Patent: Oct. 21, 1997

[54] THIENITHIAZINE DERIVATIVES

[75] Inventors: Dieter Binder; Josef Weinberger, both of Vienna; Michael Pyerin, Brunn am Gebirge, all of Austria

[73] Assignee: Chemisch Pharmazeutische Forschungsgesellschaft m.b.H., Linz, Austria

[21] Appl. No.: 355,549

[22] Filed: Dec. 14, 1994

[30] Foreign Application Priority Data

May 18, 1991 [AT] Austria ................................. A1026/94
Dec. 14, 1993 [AT] Austria ................................. A2530/93
Dec. 14, 1993 [AT] Austria ................................. A2531/93

[51] Int. Cl.⁶ .................... C07D 513/04; A61K 31/54
[52] U.S. Cl. ............................... 514/226.5; 544/48
[58] Field of Search ..................... 544/48; 514/226.5

[56] References Cited

U.S. PATENT DOCUMENTS 4,180,662  12/1979  Pfister et al. .......................... 544/48

OTHER PUBLICATIONS

Pfister et al, Chemical Abstracts, vol. 101, entry 38464 (1984).
Tanaka et al, Chemical Abstracts, vol. 111, entry 166771 (1989).
Hitzenberger et al, Chemical Abstracts, vol. 115, entry 21532 (1990).
Sawa et al, Chemical Abstracts, vol. 119, entry 173510 (1993).
Unseld et al, Chemical Abstracts, vol. 121, entry 244967 (1993).
Chemical Abstracts, vol. 111, col. 166771n (1989). Tanaka et al.
Chemical Abstracts, vol. 115, col. 21532h (1991). Hitzenberger et al.

*Primary Examiner*—John M. Ford
*Attorney, Agent, or Firm*—Wenderoth, Lind & Ponack

[57] ABSTRACT

Thienothiazine derivatives of the formula

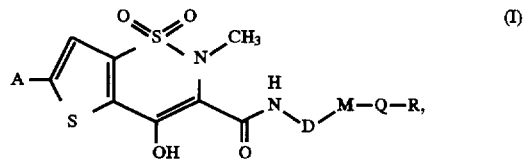

are provided. These derivatives are useful for the treatment of inflammation and pain.

8 Claims, No Drawings

THIENITHIAZINE DERIVATIVES

The present invention relates to novel, therapeutically valuable thienothiazine derivatives of the formula

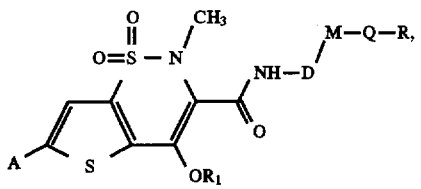

in which:

A is lower alkyl, perfluorinated lower alkyl, lower alkoxy, halogen, nitro, cyano or a mono- or polycyclic 5–12-membered, optionally partially hydrogenated aryl or heteroaryl radical with 1–4 hetero atoms such as O, S and N, which can optionally be substituted by lower alkyl, perfluoro-lower-alkyl, aryl, heteroaryl, substituted aryl, substituted heteroaryl, halogen, lower alkoxy, aryloxy, substituted aryloxy, heteroaryloxy, substituted heteroaryloxy and nitro, in which the mentioned substituents in the substituted aryl, substituted heteroaryl, substituted aryloxy and substituted heteroaryloxy are halogen, lower alkyl, perfluoro-lower-alkyl, lower alkoxy and the like;

D is a 2-pyridyl radical or a radical

where

X and Y are, independently of one another, CH, $NR^6$, O or S with $R^6$ being hydrogen or lower alkyl, M is a single bond, a straight-chain or branched carbon chain with 1–12 carbon atoms in the chain, it being possible for this chain to contain one or more double and/or triple bonds and/or one or more hetero atoms such as O, S and N, or is a 5–12-membered mono- or polycyclic, optionally partially hydrogenated aryl or heteroaryl radical with 1–4 hereto atoms such as O, S and N, which can be substituted by halogen, lower alkyl or lower alkoxy;

Q is a single bond or a hetero atom such as O, S and N;

R is hydrogen, a 5–12-membered mono- or polycyclic aryl or heteroaryl radical with 1–4 hetero atoms such as O, S and N, which can optionally be partially hydrogenated, or else can be substituted one or more times by halogen, lower alkyl or lower alkoxy; and $R_1$ is hydrogen or

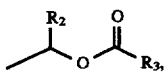

in which $R_2$ is lower alkyl and $R_3$ is lower alkyl, aryl or —$OR_4$ with $R_4$ being lower alkyl, cycloalkyl with 4–8 carbon atoms or aryl; and their pharmaceutically utilizable salts.

The present invention further relates to a process for the preparation of compounds of the formula (I), which is characterized in that a compound of the general formula

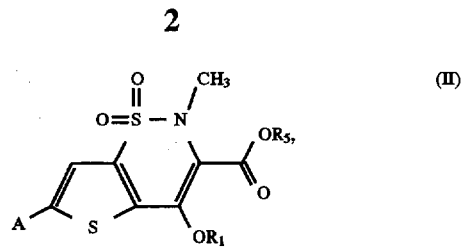

in which $R_1$ is hydrogen, $R_5$ is lower alkyl and A has the above meaning, is reacted with a compound of the formula

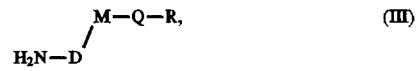

in which D, M, Q and R have the above meaning, and the compounds of the general formula (I) obtained in this way are, for $R_1$=hydrogen, optionally converted into their pharmaceutically utilizable salts or reacted with a compound of the

in which Z is chlorine or bromine and $R_2$ and $R_3$ have the above meaning, to give the compounds of the general formula (I) with $R_1$ not hydrogen.

The term "aryl" used above can mean, for example, phenyl, naphthyl, and the like and the term "heteroaryl" can mean, for example, thienyl, furyl, pyrrolyl, pyridinyl, pyrimidinyl, pyridazinyl, imidazolyl, pyrazolyl, thiazolyl, oxazolyl, oxadiazolyl, thiadiazolyl, pyranyl, thiopyranyl, benzo[b]furyl, benzo[b]thienyl, quinolinyl, isoquinolinyl and the like.

The term "halogen" used above means fluorine, chlorine, bromine or iodine.

The term "lower alkyl" used above means a straight-chain or branched alkyl radical with 1–4 carbon atoms, for example methyl, ethyl, n- and i-propyl, n-, i- and t-butyl.

The term "lower alkoxy" used above means a straight-chain or branched alkoxyradical with 1–4 carbon atoms, for example methoxy, ethoxy, n- and i-propoxy, n-, i- and t-butoxy.

The reactions according to the invention are best carried out by either

A) dissolving the compound of the general formula (II) in an inert solvent, such as diethyl ether, THF, dioxane, toluene, benzene etc., and adding at a temperature between −20° C. and 100° C. one equivalent of a strong base such as butyllithium or LDA, adding to this salt solution 1–10 equivalents of a compound of the general formula (III), adding at least one further equivalent of the strong base, and stirring at −20° C. to 100° C. for between 0.5 and 60 hours, or B) heating a solution of the compounds (II) and (III) in an inert, high-boiling solvent, such as toluene, xylene, pyridine, quinoline, DMF, DMSO or BMPA etc., at between 100° C. and 200° C. for 1–30 hours, and the compounds of the general formula (I) obtained in this way are, in the case where $R_1$ is not hydrogen, either C) reacted in an inert solvent, such as acetone, DMF, DMSO or HMPA, with at least one equivalent of a base, such as NaH, sodium trimethylsilanolate and the like, at room temperature, and stirred with at least one equivalent of a compound of the formula (IV) at 0°–150° C. for 1–100 hours, or D) stirred in a basic solvent such a triethylamine, pyridine, quinoline and the like with at least one equivalent of a compound of the formula (IV) at 0°–150° C. for 1–100 hours.

The compounds of the formula (I) with $R_1$=hydrogen which are obtained in this reaction are acidic compounds and can be converted in a conventional way with inorganic or organic bases into their pharmaceutically suitable salts.

The salt formation can be carried out, for example, by dissolving the compounds of the formula (I) in a suitable solvent, for example water, a lower aliphatic alcohol, THF, dioxane, benzene, diethyl ether, DMF or DMSO, adding an equivalent amount of the required base, ensuring thorough mixing and, after the salt formation is complete, stripping off the solvent in vacuo. The salts can be recrystallized where appropriate after the isolation.

Examples of pharmaceutically utilizable salts are metal salts, in particular alkali metal and alkaline earth metal salts, such as sodium, potassium, magnesium or calcium salts. Other pharmaceutical salts, are, for example, readily crystallizing ammonium salts. The latter are derived from ammonia or from organic amines, for example mono-, di- or tri-lower-(alkyl, cycloalkyl or hydroxyalkyl) amines, lower alkylenediamines or (hydroxy-lower-alkyl or aryl-lower-alkyl)-lower-alkylammonium bases, for example methylamine, diethylamine, triethylamine, dicyclohexylamine, triethanolamine, ethylene-aliamine, tris (hydroxymethyl) aminomethane, benzyltrimethylammonium hydroxide and the like. The compounds of the general formula (II), (III) and (IV) are known from the literature or can be prepared in analogy thereto by conventional methods which are familiar to the skilled worker.

The compounds of the general formula (I) according to the invention and their salts have oral activity and surprisingly show, by comparison with 6-chloro-2-methyl-N-(2-pyridyl)-2H-thieno[2,3-e]-1,2-thiazine-3-carboxamide 1,1-dioxide ("LORNOXICAM", U.S. Pat. No. 4,180,662), a significantly increased inhibition of 5-lipoxygenase with very substantial retention of the cyclooxygenase inhibition.

They are therefore particularly suitable for the treatment of disorders partly caused by the natural product of 5-lipoxygenase, namely leucotriene $B_4$ and the cyclooxygenase products, such as, for example, inflammation and pain associated with allergic asthma, arthritis, skin allergy, rheumatic disorders etc.

By reason of these pharmacological properties, the novel compounds can be used, alone or mixed with other active substances, in the form of conventional pharmaceutical preparations as medicines for the treatment of disorders which are cured or alleviated by inhibition of 5-lipoxygenase and cyclooxygenase.

The invention furthermore relates to medicines which are used, for example, in the form of pharmaceutical products which contain the compounds of the formula (I) according to the invention and their salts mixed with a pharmaceutical organic or inorganic vehicle suitable for oral, enteral, parenteral and topical administration, for example water, gelatin, gum arabic, lactose, starch, magnesium stearate, talc, vegetable oils, polyalkylene glycols, petrolatum or the like.

The pharmaceutical products can be in solid form, for example as tablets, film-coated tablets, sugar-coated tablets, suppositories, capsules, microcapsules or in liquid form, for example as solutions, solutions for injection, suspensions or emulsions, or in compositions with delayed release of the active substance.

They are, where appropriate, sterilized and/or contain ancillary substances such as preservatives, stabilizers or emulsifiers, salts to alter the osmotic pressure or buffers.

In particular, pharmaceutical products may contain the compounds according to the invention in combination with other therapeutically valuable substances. The compounds according to the invention can be formulated with the latter together with the abovementioned ancillary substances and/or vehicles to give combination products.

The novel compounds may be present in the pharmaceutical compositions according to the invention in an amount of about 4–200 mg per tablet, the remainder being a pharmaceutically acceptable bulking agent.

A suitable dose for the administration of the novel compounds is about 1–200 mg/kg per day, but other doses are also suitable, depending on the condition of the patient to be treated. The novel compounds can be administered in several doses and by the oral route.

The following examples explain the invention in more detail without intending to restrict the latter thereto:

EXAMPLE 1

6-Chloro-4-hydroxy-2-methyl-N-(2-thiazolyl)-2H-thieno[2,3-e]-1,2-thiazine-3-carboxamide 1,1-dioxide 1.32 g (4.25 mmol) of methyl 6-chloro-4-hydroxy-2-methyl-2H-thieno[2,3-e]-1,2-thiazine-3-carboxylate 1,1-dioxide and 0.47 g (4.30 mmol) of 2-thiazolamine are heated to boiling in 12 ml of abs. xylene for 17.5 h. After the solvent has been stripped off, the crude product is digested with 5×20 ml of ice-cold diethyl ether, taken up in 1N NaOH solution, filtered hot with active charcoal and acidified, and the precipitate is filtered off and dried.

Yield: 0.175 g yellow crystals (10.94% of theory)

M.p.: 223°–225° C. ($H_2O$)

TLC: Bz/Dx/MeOH 10:1:1 Rf: 0.68

$^1$H-NMR: (DMSO-$d_6$) δ (ppm)=7.66 (s; 1H, Thio-H7); 7.60 (d, 1H, Thaz-H5); 7.22 (d; 1H, Thaz-H4); 2.96 (s; 3H, N—$CH_3$)

$^{13}$C-NMR: (DMSO-$d_6$) δ (ppm)=166.09; 164.78; 156.45; 138.41; 136.91; 135.23; 127.29; 123.00; 112.95; 111.92; 38.82

EXAMPLE 2

6-Chloro-4-hydroxy-2-methyl-N-(4phenyl-2-thiazolyl)-2H-thieno[2,3-e]-1,2-thiazine-3-carboxamide 1,1-dioxide 1.37 g (4.417 mmol) of methyl 6-chloro-4-hydroxy-2-methyl-2H-thieno[2,3-e]-1,2-thiazine-3-carboxylate 1,1-dioxide and 0.78 g (4.426 mmol) of 4-phenyl-2-thiazolamine are heated to boiling in 12.6 ml of abs. xylene. After 3.5 h and 5.5 h. on each occasion 0.4 g (2.269 mmol) of 4-phenyl-2-thiazolamine is added. The solvent is stripped off after 6 h. The crude product is digested with 3×20 ml of ice-cold diethyl ether, washed with hot ethyl alcohol and recrystallized from methylene chloride/active charcoal.

Yield: 1.15 g of yellow crystals (57.5% of theory)

M.p.: 241°–244° C. ($CH_2Cl_2$)

TLC: $CH_2Cl_2$/MeOH 40:1 Rf: 0.30

$^1$H-NMR: (DMSO-$d_6$) δ (ppm)=7.88 (d; 2H, Ph-H2,6); 7.68 (s; 1H, Thio-H7); 7.60 (s; 1H, Thiaz-H5); 7.54–7.33 (m; 3H, Ph-H3, 4,5); 2.94 (s; 3H, N—$CH_3$)

$^{13}$C-NMR: (DMSO-$d_6$) δ (ppm)=165.58; 161.93; 155.16; 142.72; 136.93; 136.39; 135.50; 131.11; 128.84; 128.66; 125.77; 122.77; 111.11; 108.08; 38.78

EXAMPLE 3

6-(2-Furyl)-4-hydroxy-2-methyl-N-(4-phenyl-2thiazolyl)-2H-thieno[2,3-e]-1,2-thiazine-3-carboxamide 1,1-dioxide 0.49 g (1.459 mmol) of methyl 6-(2-furyl)-4-hydroxy-2-methyl-2H-thieno[2,3-e]-1,2-thiazine-3-carboxylate 1,1- dioxide and 0.77 g (4.386 mmol) of 4-phenyl-2-thiazolamine are heated to boiling in 5 ml of abs. xylene for 6 h. After the solvent has been stripped off, the crude product is digested with 3×10 ml of ice-cold ethanol and recrystallized from dichloromethane/active charcoal.

Yield: 0.34 g of yellow crystals (48.0% of theory)

M.p.: decomposition above 240° C. ($CH_2Cl_2$)

TLC: $CH_2Cl_2$/MeOH 50:1 Rf: 0.23 Bz/Dx/MeOH10:1:1 Rf: 0.71

$^1$H-NMR: (DMSO-$d_6$) δ (ppm)=7.93–7.81 (m, 4H, Thio-H7, Ph-H2,6, Fu-H5); 7.64 (s, 1H, Thaz-H5); 7.53–7.31 (m, 3H, Ph-H3, 4,5); 7.22 (d, 1H, Fu-H3); 6.71 (dd, 1H, Fu-H4); 2.98 (s; 3H, N—$CH_3$)

$^{13}$C-NMR: (DMSO-$d_6$) δ (ppm)=165.71; 161.26; 155.92; 146.93; 144.46; 143.85; 138.62; 138.52; 134.60; 131.82; 128.84; 128.48; 125.77; 117.53; 112.90; 110.77; 109.42; 108.10; 38.93

The starting material can be prepared as follows:

2-Cyano-1-(2-furyl)ethenyl 4-methylbenzenesulphonate 67.78 g (356 mmol) of p-toluenesulphonyl chloride in 100 ml of absolute dichloromethane are added dropwise to 45.75 g (339 mmol) of b-oxo-2-furanpropanenitrile and 47.95 g (474 mmol) of N-methylmorpholine in 100 ml of absolute dichloromethane at −5° to 0° C., and the mixture is then stirred for one hour. The solvent is stripped off, the residue is partitioned between 500 ml of ethyl acetate and 400 ml of 1N hydrochloric acid, and the aqueous phase is extracted with 6×150 ml of ethyl acetate. The combined extracts are dried over $Na_2SO_4$/active charcoal and filtered, and the extractant is removed by distillation. The resulting solid is recrystallized from 150 ml of toluene/active charcoal.

Yield: 92.48 g of colourless crystals (94% of theory)

TLC: solvent Bz:$Et_2O$=10:1; 0.65

M.p.: 109°–111° C. (toluene)

$^1$H-NMR: (DMSO-$d_6$) d(ppm): 8.00–7.85 (m, 3H, Bz-H2,6, Fu-H5); 7.60–7.48 (m, 2H, Bz-H3,5) 6.74 (dd, 1H, Fu-H3*); 6.57 (dd, 1H, Fu-H4*); 6.33 (s, 1H, C$\underline{H}$—CN); 2.45 (s, 3H, C$\underline{H}_3$)

$^{13}$C-NMR: (DMSO-$d_6$) d(ppm): 150.2; 147.7; 146.8; 145.4; 131.1; 130.4; 128.4; 115.9; 114.4; 113.1; 87.3; 21.2

Methyl 3-amino-5-(2-furyl)-2-thiophenecarboxylate hydrochloride 32.75 g (309 mmol) of methyl thioglycolate are added to 16.75 g (309 mmol) of sodium methanolate in 750 ml of absolute methanol at 15°–20° C., and the mixture is stirred at room temperature for 20 minutes. Subsequently 74.38 g (257 mmol) of 2-cyano-1-(2-furyl)ethenyl 4-methylbenzenesulphonate are added in one portion, and the mixture is stirred for a further 2½ hours. After the solvent has been stripped off, the residue is partitioned between 500 ml of water and 400 ml of diethyl ether, a further extraction with 200 ml of diethyl ether is carried out, and the organic phase is dried over $Na_2SO_4$/active charcoal, filtered and concentrated to 400 ml. Then, while cooling in ice and stirring vigorously, dry hydrogen chloride is passed in for one hour, the mixture is cooled to −20° C., and the precipitated hydrochloride is filtered off and digested with 2×100 ml of dry diethyl ether.

Yield: 37.74 g of colourless crystals (57% of theory)

TLC (amine): solvent Bz:$Et_2O$=5:1; 0.4

M.p.: 134°–136° C. (Ether)

$^1$H-NMR: (DMSO-$d_6$) d(ppm): 7.79 (dd, 1H, Fu-H5); 7.46 ($s_{broad}$, 3H, N$\underline{H}_3$Cl); 6.90 (dd, 1H, Fu-H3); 6.87 (s, 1H, Th-H4); 6.62 (dd, 1H, Fu-H4); 3.72 (s, 3H, C$\underline{H}_3$)

$^{13}$C-NMR: (DMSO-$d_6$) d(ppm): 164.0; 154.2; 148.0; 144.1; 136.9; 115.3; 112.7; 108.6; 97.5; 51.3

Methyl 3-chlorosulphonyl-5-(2-furyl)-2-thiophenecarboxylate 11.29 g (164 mmol) of sodium nitrite in 16 ml of water are introduced under the surface of the liquid into a suspension of 35.42 g (136 mmol) of methyl 3-amino-5-(2-furyl)-2-thiophenecarboxylate hydrochloride in 215 ml of concentrated hydrochloric acid at −12° C. over the course of ½ hour, and the mixture is thoroughly stirred for one hour. In parallel to this, 47 ml of an aqueous copper(II) chloride solution which is saturated at room temperature are added, while cooling in ice in a tall beaker, to 725 ml of a solution, which is saturated at 0° C., of sulphur dioxide in glacial acetic acid (~40% strength). Added to this mixture all at once, the suspension of the diazonium salt warms to 30° C. The volume loss caused thereby is immediately compensated with 70 ml of the sulphur dioxide solution, and the mixture is stirred at room temperature for a total of 2 hours. The reaction mixture is poured into 2 l of ice-water, and the resulting precipitate is filtered off and digested three times with 300 ml of cold water each time. The solid is partitioned between 400 ml of water and 300 ml of dichloromethane and extracted three times more with 200 ml of dichloromethane each time. The organic phase is dried over $Na_2SO_4$/active charcoal and filtered, and the solvent is stripped off.

Yield: 38.46 g of brown crystals (92% of theory)

TLC: solvent Bz:$Et_2O$=10:1; 0.7

M.p.: 133°–136° C. (decomposition)

$^1$H-NMR: (CDCl$_3$) d(ppm): 7.68 (s, 1H, Th-H4); 7.51 (dd, 1H, Fu-H5); 6.77 (dd, 1H, Fu-H3); 6.53 (dd, 1H, Fu-H4); 3.99 (s, 3H, C$\underline{H}_3$)

$_{13}$C-NMR: (CDCl$_3$) d(ppm): 158.7; 146.1; 144.4; 144.1; 137.5; 131.5; 123.3; 112.5; 109.4; 53.1

Methyl 5-(2-furyl)-3-[N-(methoxycarbonylmethyl) sulphamoyl]-2-thiophenecarboxylate 22.69 g (224 mmol) of triethylamine are added dropwise to a suspension of 30.57 g (99.7 mmol) of methyl 3-chlorosulphonyl-5-(2-furyl)-2-thiophenecarboxylate and 15.64 g (125 mmol) of glycine methyl ester hydrochloride in 255 ml of absolute methanol at 0° C., and the mixture is stirred for one hour. The reaction mixture is poured into 750 ml of ice-cold 2N hydrochloric acid and cooled to about −15° C., the resulting crystals are filtered off and digested three times with 200 ml of ice-cold water each time. The crude product is recrystallized from methanol/active charcoal.

Yield: 29.61 g of brown crystals (83% of theory)

TLC: solvent Bz:$Et_2O$=10:1; 0.3

M.p.: 102°–105° C. (methanol)

$^1$H-NMR: (CDCl$_3$) d(ppm): 7.60 (s, 1H, Th-H4); 7.48 (dd, 1H, Fu-H5); 6.91 (t, 1H, N$\underline{H}$); 6.73 (dd, 1H, Fu-H3); 6.51 (dd, 1H, Fu-H4); 3.95 (s, 3H, Th-COOC$\underline{H}_3$); 3.92 (d, 2H, C$\underline{H}_2$); 3.62 (s, 3H, $CH_2$-COOOC$\underline{H}_3$)

$^{13}$C-NMR: (CDCl$_3$) d(ppm): 168.9; 160.9; 146.8; 145.0; 143.7; 137.6; 127.5; 124.3; 112.3; 108.9; 53.0; 52.3; 44.5

Methyl 6-(2-furyl)-2H-thieno[2,3-e]-1,2-thiazine-3-carboxylate 1,1-dioxide 32.11 g (89.3 mmol) of methyl 5-(2-furyl)-3-[N-(methoxycarbonylmethyl)sulphamoyl]-2- thiophenecarboxylate in 330 ml of absolute tetrahydrofuran are added dropwise to 23.06 g (206 mmol) of potassium tert-butanolate in 265 ml of absolute tetrahydrofuran at −10° to −5° C. The reaction mixture is stirred for half an hour, and 1.2 l of ice-cold 2N hydrochloric acid are added all at once. The crude product is filtered off and digested three times with 250 ml of cold water each time and once with 100 ml of cold methanol.

Yield: 23.66 g of orange-brown crystals (81% of theory)

TLC: solvent $CH_2Cl_2$:MeOH=40:1; 0.4

M.p.: 215°–222° C. (decomposition, methanol)

$^1$H-NMR: (DMSO-$d_6$) d(ppm): 7.88 (s, 1H, TT-H7); 7.87 (d, 1H, Fu-H5); 7.22 (d, 1H, Fu-H3); 6.70 (dd, 1H, Fu-H4); 3.89 (s, 3H, C$\underline{H}_3$)

$^{13}$C-NMR: (DMSO-$d_6$) d(ppm): 166.8; 149.7; 146.8; 144.6; 140.4; 138.6; 132.0; 116.2; 112.9; 109.7; 104.9; 52.7

Methyl 6-(2furyl)-2-methyl-2H-thieno[2,3-e]-1,2-thiazine-3-carboxylate 1,1-dioxide 22.81 g (69.7 mmol) of methyl 6-(2-furyl)-2H-thieno[2,3-e]-1,2-thiazine-3-carboxylate 1,1-dioxide in 160 ml of absolute DMF are added dropwise to a suspension of 1.84 g (76.7 mmol) of sodium hydride in 40 ml of absolute DMF at −10° C. to −7° C., and the mixture is stirred for one hour. 11.87 g (83.6 mmol) of iodomethane are added to the resulting solution, and the mixture is stirred at room temperature for 20 hours. Hydrolysis is carried out with 1 l of ice-cold 2N hydrochloric acid. The resulting precipitate is filtered off and digested twice with 100 ml of cold water each time and once with 70 ml of cold methanol. The crude product is recrystallized from 250 ml of dioxane/active charcoal and digested with 20 ml of cold acetone.

Yield: 19.73 g of yellow crystals (83% of theory)

TLC: solvent Bz:MeOH=10:1; 0.65

M.p.: 219°–222° C. (decomposition, dioxane)

$^1$H-NMR: (DMSO-$d_6$) d(ppm)): 7.91 (s, 1H, TT-H7); 7.87 (d, 1H, Fu-H5); 7.26 (d, 1H, Fu-H3); 6.71 (dd, 1H, Fu-H4); 3.85 (s, 3H, OC$\underline{H}_3$); 2.95 (s, 3H, NC$\underline{H}_3$);

$^{13}$C-NMR: (DMSO-$d_6$) d(ppm): 167.0; 153.5; 146.6; 144.8; 139.8; 139.4; 131.3; 117.5; 113.0; 110.1; 109.1; 52.7; 38.4

EXAMPLE 4

6-Chloro-N-{4-[5-(4-fluorophenoxy)-2-furanyl]-2-thiazolyl}-4-hydroxy-2-methyl-2H-thieno[2,3-e]-1,2-thiazine-3-carboxamide 1,1-dioxide 0.446 g (1.44 mmol) of methyl 6-chloro-4-hydroxy-2-methyl-2H-thieno[2,3-e]-1,2-thiazine-3-carboxylate 1,1-dioxide and 0.404 g (1.46 mmol) of 4-[5-(4-fluoro-phenoxy)-2-furanyl]-2-thiazolamine are heated to boiling in 4 ml of absolute xylene. After 4.5 h, the suspension is cooled, and the product is filtered off, digested several times with diethyl ether and recrystallized from toluene.

Yield: 0.373 g of yellow crystals (46.6% of theory)

M.p.: decomposition above 220° C. (Et$_2$O)

TLC: CH$_2$Cl$_2$/MeOH 5:1 Rf: 0.5

$^1$H-NMR: (DMSO-$d_6$) δ (ppm):=7.87 (d; 1H, Fu-H5); 7.81 (s; 1H, Th-H7); 7.23 (s; 1H, Thiaz-H5); 7.22–7.07 (m; 5H, Ph-H2,3,5,6); 6.80 (d; 1H, Fu-H3, $^3J_{H,H4}$=3.3 Hz); 6.65 (m; 1H, Fu-H4); 5.84 (d; 1H, Fu-H4, $^3J_{H,H4}$=3.3 Hz); 2.98 (s; 3H, —N—CH$_3$)

$^{13}$C-NMR: (DMSO-$d_6$) δ (ppm)=164.88 (s; C=O); 160.35 (s; Th-C4); 158.65 (d; Ph-C4, $^1J_{C,F}$=240.6 Hz); 155.73 (s; Thiaz-C2, Fu-C5*); 152.09 (d; Ph-C1, $^4J_{C,F}$=2.3 Hz); 141.07 (s; Fu-C2); 137.50 (s; Th-C4a); 137.00 (s; Th-C7a, Thiaz-C4)*; 135.28 (s; Th-C6); 122.85 (d; Th-C7); 118.88 (dd; Ph-C2,6, $^3J_{C,F}$=8.7 Hz); 116.69 (dd; Ph-C3,5, $^2J_{C,F}$=23.7 Hz); 110.10 (s; Th-C3); 108.54 (d; Fu-C3); 106.08 (s; Thiaz-C5); 91.14 (d; Fu-C4); 39.09 (q; —N—C$\underline{H}_3$)

The starting material can be prepared as follows:

5-(4-Fluorophenoxy)-2-furancarboxylic acid 10.03 g (48.65 mmol) of 5-(4-fluorophenoxy)-2-furancarbaldehyde are suspended in 200 ml of aqueous 4N sodium hydroxide solution and, at 65° C., a solution of 18.10 g (106.6 mmol) of silver nitrate in 100 ml of distilled water is added as quickly as possible. After 90 min, the hot solution is filtered through Hyflo and washed 3× with 40 ml of hot aqueous 4N sodium hydroxide solution each time. The filtrate is adjusted at 0° C. to pH 3 with 4N aqueous hydrochloric acid and extracted 7× with 100 ml of diethyl ether each time. The combined organic phases are concentrated to about 50 ml, and the precipitated product is taken up in 300 ml of half-saturated sodium bicarbonate solution. The organic phase is separated off and the aqueous phase is extracted 2× with 25 ml of diethyl ether each time. The aqueous phase is adjusted at 0° C. to pH 3 with concentrated hydrochloric acid and extracted 5× with 50 ml of diethyl ether each time, and the combined organic phases are washed 2× with 20 ml of 2N sodium hydroxide solution each time and once with 20 ml of water. They are then dried over sodium sulphate and filtered, and the solvent is stripped off.

Yield: 7.48 g of colourless crystals (69.2% of theory)

M.p.: decomposition above 110° C. (Et$_2$O)

TLC: Bz/EA8:1 Rf: 0.7

$^1$H-NMR: (DMSO-$d_6$) δ (ppm)=7.34–7.25 (m; 4H, Ph-H2,3,5,6); 7.21 (d; 1H, Fu-H4, $^3J_{H,H3}$=4 Hz); 5.78 (d; 1H, Fu-H3, $^3J_{H,H4}$=4 Hz)

$^{13}$C-NMR: (DMSO-$d_6$) δ (ppm)=159.08 (d; Ph-C4, $^1J_{C,F}$=241.4 Hz); 158.82 (s; Fu-C2); 158.69 (d, Fu-C4); 150.77 (d, Ph-C1, $^4J_{C,F}$=2.4 Hz); 136.68 (s; Fu-C5); 120.06 (dd; Ph-C2,6, $^3J_{C,F}$=8.7 Hz); 116.75 (dd; Ph-C3,5, $^2J_{C,F}$=23.8 Hz); 90.17 (d, Fu-C3)

2-(4-Fluorophenoxy)furan 7.45 g (33.53 mmol) of 5-(4-fluorophenoxy)-2-furancarboxylic acid are heated to 110° C. in a kugelrohr under 38 mbar, whereupon the resulting product distils into the receiver.

Yield: 4.54 g of yellowish liquid (76.0% of theory)

B.p.: 95°–100° C./38 mbar $n_D^{20}$ : 1.5159

TLC: Bz/EA8:1 Rf: 0.7

$^1$H-NMR: (DMSO-$d_6$) δ (ppm)=7.32 (d; 1H, Fu-H5, $^3J_{H,H4}$=2 Hz); 7.25–7.05 (m; 4H, Ph-H2,3,5,6); 6.46 (dd; 1H, Fu-H4, $^3J_{H,H3}$=4 Hz, $^3J_{H,H5}$=2 Hz); 5.74 (d; 1H, Fu-H3, $^3J_{H,H3}$=4 Hz)

$^{13}$C-NMR: (DMSO-$d_6$) δ (ppm)=158.40 (d; Ph-C4, $^1J_{C,F}$=240.0 Hz); 155.87 (s; Fu-C2); 152.40 (d, Ph-C1, $^4J_{C,F}$=2.3 Hz); 135.79 (d; Fu-C5); 118.84 (dd; Ph-C2,6, $^3J_{C,F}$=8.6 Hz); 116.45 (dd; Ph-C3,5, $^2J_{C,F}$=23.7 Hz); 111.37 (d; Fu-C4); 89.16 (d; Fu-C3)

1-[5-(4-Fluorophenoxy)-2-furanyl]-2-chloroethanone 1.86 g (29.08 mmol) of n-butyllithium (2.5N in n-hexane) are added dropwise to 5.18 g (29.08 mmol) of 2-(4- fluorophenoxy)furan in 40 ml of absolute tetrahydro-furan at −75° C., and the mixture is stirred for 2.5 h. Then 6.14 g (50.51 mmol) of 2-chloro-N,N-dimethylacetamide in 30 ml of absolute tetrahydrofuran are added at −75° C. After 60 min, the mixture is poured into 200 ml of ice-water, neutralized at 0° C. with 2N hydrochloric acid and extracted 5× with 40 ml of ethyl acetate each time. The combined organic phases are washed 2× with 20 ml of water each time, dried over sodium sulphate and filtered, and the solvent is stripped off. The product is purified by column chromatography (360 g of silica gel 60; solvent: toluene) and recrystallized from diisopropyl ether.

Yield: 3.0 g of colourless crystals (41.1% of theory)

M.p.: 99°–100° C. (DIPE)

TLC: Bz/EA8:1 Rf: 0.7

$^1$H-NMR: (CDCl$_3$) δ (ppm)=7.31 (d; 1H, Fu-H4, $^3J_{H,H3}$=3.8 Hz); 7.21–7.02 (m; 4H, Ph-H2,3,5,6); 5.51 (d; 1H, Fu-H3, $^3J_{H,H4}$=3.8 Hz); 4.45 (s; 2H, —CH$_2$Cl) $^{13}$C-NMR: (CDCl$_3$) δ (ppm)=178.32 (s; C=O); 161.63 (s; Fu-C5); 159.95 (d; Ph-C4, $^1J_{C,F}$=245.0 Hz); 149.92 (d, Ph-C1, $^4J_{C,F}$=3.4 Hz); 142.13 (s; Fu-C2); 122.43 (d; Fu-C4); 120.46 (dd; Ph-C2,6, $^3J_{C,F}$=8.5 Hz); 116.66 (dd; Ph-C3,5, $^2J_{C,F}$=23.8 Hz); 89.59 (d; Fu-C3); 44.17 (t; —CH$_2$—Cl)

4-[5-(4-Fluorophenoxy)-2-furanyl]-2-thiazolamine 2.46 g (9.65 mmol) of 1-[5-(4-fluorophenoxy)-2-furanyl]-2-chloroethanone, 0.758 g (10.00 mmol) of thiourea and 1.33 g (9.62 mmol) of potassium carbonate are heated to boiling in 25 ml of absolute ethanol. After 60 min, the cooled solution is poured into 150 ml of water and extracted 5× with 40 ml of ethyl acetate each time. The combined organic phases are washed once with 20 ml of water, dried over sodium sulphate and filtered, and the solvent is stripped off. The product is recrystallized from diisopropyl ether.

Yield: 1.46 g of colourless crystals (54.7% of theory)

M.p.: 108°–110° C. (DIPE)

TLC: EA Rf: 0.8 Bz/EA8:1 Rf: 0.1

$^1$H-NMR: (DMSO-d$_6$) δ (ppm)=7.32–7.08 (m; 4H, Ph-H2,3,5,6); 6.60 (s; 1H, Thiaz-H5); 6.52 (d; 1H, Fu-H3, $^3J_{H,H4}$=3.3 Hz); 5.78 (d; 1H, Fu-H4, $^3J_{H,H3}$=3.3 Hz)

$^{13}$C-NMR: (DMSO-d$_6$) δ (ppm)=168.75 (s; Thiaz-C2); 158.57 (d; Ph-C4, $^1J_{C,F}$=240.3 Hz); 154.98 (s; Fu-C5); 152.31 (d; Ph-C1, $^4J_{C,F}$=2.3 Hz); 143.34 (s; Fu-C2); 140.99 (s; Thiaz-C4); 118.67 (dd; Ph-C2,6, $^3J_{C,F}$=8.6 Hz); 116.61 (dd; Ph-C3,5, $^2J_{C,F}$=23.7 Hz); 107.09 (d; Fu-C3); 99.75 (d; Thiaz-C5); 90.94 (d; Fu-C4)

EXAMPLE 5

N-{4[5-(4-Fluorophenoxy)-2-furanyl]-2-thiazolyl}-6-(2-furanyl)-4-hydroxy-2-methyl-2H-thieno[2,3-]-1,2-thiazine-3-carboxamide 1,1-dioxide 0.339 g (0.99 mmol) of methyl 6-(2-furanyl)-4-hydroxy-2-methyl-2H-thieno[2,3-e]-1,2-thiazine-3-carboxylate 1,1-dioxide and 0.398 g (1.44 mmol) of 4-[5-(4-fluorophenoxy)-2-furanyl]-2-thiazolamine are heated to boiling in 3 ml of absolute xylene. After 4.5 h, the suspension is cooled, and the precipitated product is filtered off, digested several times with diethyl ether and recrystallized from dimethyl sulphoxide/acetone 10:1.

Yield: 0.30 g of yellow crystals (51.7% of theory)

M.p.: decomposition above 243° C. (DMSO)

TLC: CH$_2$Cl$_2$/MeOH 5:1 Rf: 0.8

$^1$H-NMR: (DMSO-d$_6$) δ (ppm)=7.82 (m; 1H, Fu-H5); 7.81 (s; 1H, Th-H7); 7.23 (s; 1H, Thiaz-H5); 7.22–7.07 (m; 3H, Ph-H2,3,5,6, Fu-H3); 6.80 (d; 1H, ThiazFu-H3, $^2J_{H,H4}$=3.3 Hz); 6.65 (m; 1H, Fu-H4); 5.84 (d; 1H, ThiazFu-H4, $^2J_{H,H3}$=3.4 Hz); 2.98 (s; 3H, —N—CH$_3$)

$^{13}$C-NMR: (DMSO-d$_6$) δ (ppm)=164.99 (s; C=O); 159.01 (s; Thiaz-C2); 158.63 (d; Ph-C4, $^1J_{C,F}$=240.3 Hz); 157.22 (s; Thiaz-Fu-C5); 155.61 (s; Th-C4); 152.11 (s; Ph-C1); 147.01 (s; Fu-C2); 144.43 (s; Fu-C5); 141.51 (s; ThiazFu-C2); 138.56 (s; Th-C7a*); 138.43 (s; Thiaz-C4*); 137.67 (s; Th-C4a); 135.18 (s; Th-C6*); 118.85 (dd; Ph-C2,6, $^3J_{C,F}$=8.7 Hz); 117.57 (d; Th-C7); 116.68 (dd; Ph-C3,5, $^2J_{C,F}$=23.7 Hz); 112.90 (s; Fu-C3); 109.75 (s; Th-C3); 109.31 (d; Fu-C4*); 108.32 (d; ThiazFu-C3*); 106.14 (d; Thiaz-C5); 91.17 (d; ThiazFu-C4); 39.08 (q; —N—CH$_3$)

EXAMPLE 6

6-Chloro-N-{4-[5-(4-fluorophenyl)-2-furanyl]-2-thiazolyl}-4-hydroxy-2-methyl-2H-thieno[2,3-e]-1,2-thiazine-3-carboxamide 1,1-dioxide 0.209 g (0.68 mmol) of methyl 6-chloro-4-hydroxy-2-methyl-2H-thieno [2,3-e]-1,2-thiazine-3-carboxylate 1,1-dioxide and 0.182 g (0.70 mmol) of 4-[5-(4-fluorophenyl)-2-furanyl]-2-thiazolamine are heated to boiling in 2.5 ml of absolute xylene for 5 h. After cooling, the precipitated product is filtered off, digested 3× with diethyl ether and recrystallized from dimethyl sulphoxide.

Yield: 0.320 g of yellow crystals (88.2% of theory)

M.p.: decomposition above 250° C. (DMSO)

TLC: EA Rf: 0.4 CH$_2$Cl$_2$/MeOH 9:1 Rf: 0.2

$^1$H-NMR: (DMSO-d$_6$) δ (ppm)=7.88 (dd; 2H, Ph-H2,6, $^3J_{H,H3(5)}$=8.4 Hz, $^3J_{H,F}$=5.6 Hz); 7.68 (S; 1H, Th-H7); 7.51 (s; 1H, Thiaz-H5); 7.35 (dd; 2H, Ph-H3,5, $^3J_{H,H2(6)}$=$^3J_{H,F}$=8.8 Hz); 7.08 (d; 1H, Fu-H3, $^3J_{H,H4}$=3.3 Hz); 6.89 (d; 1H, Fu-H4, $^3J_{H,H4}$=3.3 Hz); 2.96 (s; 3H, —N—CH$_3$)

$^{13}$C-NMR: (DMSO-d$_6$) δ (ppm)=164.85 (s; C=O); 161.66 (d; Ph-C4, $^1J_{C,F}$=245.2 Hz); 160.46 (s; Th-C4); 156.72 (s; Thiaz-C2); 152.00 (s; Fu-C5); 147.91 (s; Fu-C5); 138.08 (s; Thiaz-C4); 137.33 (s; Th-C4a); 136.92 (s; Th-C7a); 135.14 (s; Th-C6); 126.54 (d; Ph-C1, $^4J_{C,F}$=3.1 Hz); 125.74 (dd; Ph-C2,6, $^3J_{C,F}$=8.3 Hz); 122.81 (d; Th-C7); 115.95 (dd; Ph-C3,5, $^2J_{C,F}$=22.0 Hz); 109.97 (s; Th-C3); 109.38 (d; Fu-C3); 107.68 (d; Thiaz-C5*); 107.18 (d; Fu-C4*); 39.09 (q; —N—CH$_3$)

The starting material can be prepared as follows:

1-[5-(4-Fluorophenyl)-2-furanyl]-2-chloroethanone 1.60 g (21.98 mmol) of n-butyllithium (2.5N in n-hexane) are added dropwise to 4.44 g (27.41 mmol) of 2-(4-fluorophenyl)furan in 40 ml of absolute tetrahydrofuran at −75° C. After stirring for 45 min, 5.21 g (42.86 mmol) of 2-chloro-N,N-dimethylacetamide in 20 ml of absolute tetrahydrofuran are added at −75° C. After 60 min, the mixture is poured into 200 ml of ice-water, neutralized at 0° C. with 2N hydrochloric acid and extracted 6× with 60 ml of ethyl acetate each time, the combined organic phases are washed 2× with 20 ml of water each time, dried over sodium sulphate and filtered, and the solvent is stripped off. The product is purified by column chromatography (280 g of silica gel 60; solvent: PE/EA 20:1), recrystallized from ethanol and digested with diisopropyl ether.

Yield: 2.3 g of colourless crystals (35.2% of theory)

M.p.: 108°–110° C. (DIPE)

TLC: Bz/EA8:1 Rf: 0.6 PE/EA20:1 Rf: 0.1

$^1$H-NMR: (CDCl$_3$) δ (ppm)=7.77 (dd; 2H, Ph-H2,6, $^3J_{H,H3(5)}$=8.8 Hz, $^3J_{H,F}$=5.3 Hz); 7.40 (d; 1H, Fu-H3, $^3J_{H,H4}$ =3.8 Hz); 7.14 (dd; 2H, Ph-H3,5, $^3J_{H,H2(6)}=^3J_{H,F}$=8.6 Hz); 6.77 (d; 1H, Fu-H4, $^3J_{H,H3}$=3.8 Hz); 4.58 (s; 2H, —C$H_2$—Cl)

$^{13}$C-NMR: (CDCl$_3$) δ (ppm)=197.48 (s; C=O); 163.30 (d; Ph-C4, $^1J_{C,F}$=250.7 Hz); 157.57 (d; Fu-C3); 149.32 (d; Fu-C4); 127.01 (dd; Ph-C2,6, $^3J_{C,F}$=8.5 Hz); 125.17 (d, Ph-C1, $^4J_{C,F}$=3.4 Hz); 121.16 (s; Fu-C5); 116.05 (dd; Ph-C3, 5, $^2J_{C,F}$=21.2 Hz); 107.46 (s; Fu-C2); 44.80 (t; —CH$_2$—Cl)

4-[5-(4-Fluorophenyl)-2-furanyl]-2-thiazolamine 1.55 g (6.50 mmol) of 1-[5-(4-fluorophenyl)-2-furanyl]-2-chloroethanone, 0.517 g (6.79 mmol) of thiourea and 0.925 g (6.70 mmol) of potassium carbonate are heated to boiling in 7 ml of absolute ethanol. After 60 min, the suspension is poured into 150 ml of water and extracted 5× with 40 ml of ethyl acetate each time, the combined organic phases are washed 2× with 20 ml of water each time, dried over sodium sulphate and filtered, and the solvent is stripped off. The product is digested with diisopropyl ether.

Yield: 1.26 g of colourless crystals (74.6% of theory)

M.p.: 172°–173° C. (DIPE)

TLC: EA Rf: 0.8 CH$_2$Cl$_2$/EA 5:1 Rf: 0.3

$^1$H-NMR: (DMSO-d$_6$) δ (ppm)=7.85–7.71 (dd; 2H, Ph-H2,6, $^3J_{H,H3(5)}$=8.9 Hz, $^3J_{H,F}$=5.4 Hz); 7.26 (dd; 2H, Ph-H3,5, $^3J_{H,H2(6)}=^3J_{H,F}$=8.9 Hz); 6.97 (d; 1H, Fu-H3, $^3J_{H,H4}$=3.4 Hz); 6.90 (s; 1H, Thiaz-H5); 6.62 (d; 1H, Fu-H4, $^3J_{H,H3}$=3.4 Hz)

$^{13}$C-NMR: (DMSO-d$_6$) δ (ppm) 168.83 (s; Thiaz-C2); 159.05 (d; Ph-C4, $^1J_{C,F}$=250.0 Hz); 151.16 (s; Fu-C5*); 150.19 (s; Fu-C2*); 141.55 (s; Thiaz-C4); 126.87 (s; Ph-C1); 125.45 (dd; Ph-C2,6, $^3J_{C,F}$=8.2 Hz); 115 87 (dd; Ph-C3,5, $^2J_{C,F}$=22.0 Hz); 108 23 (d; Fu-C3*); 107.43 (d; Thiaz-C5*); 101.11 (d; Fu-C4)

EXAMPLE 7

N-{4-[5-(4-Fluorophenyl)-2-furanyl]-2-thiazolyl}-6-(2-furanyl)-4-hydroxy-2-methyl-2H-thieno[2,3-e]-1,2-thiazine-3-carboxmide 1,1-dioxide 0.204 g (0.60 mmol) of methyl 6-(2-furanyl)-4-hydroxy-2-methyl-2H-thieno[2,3-e]-1,2-thiazine -3-carboxylate 1,1-dioxide and 0.160 g (0.62 mmol) of 4-[5-(4-fluorophenyl)-2-furanyl]-2-thiazolamine are heated to boiling in 2.5 ml of absolute xylene for 5 h. After cooling, the precipitated product is filtered off, digested 3× with diethyl ether and recrystallized from dimethyl sulphoxide.

Yield: 0.246 g of orange crystals (72.4% of theory)

M.p.: decomposition above 250° C. (DMSO)

TLC: EA Rf: 0.3 CH$_2$Cl$_2$/MeOH 9:1 Rf: 0.3

$^1$H-NMR: (DMSO-d$_6$) δ (ppm)=7.96–7.75 (m; 4H, Fu-H5, Th-H5, Ph-H3,5); 7.53 (s; 1H, Thiaz-H5); 7.31 (dd; 2H, Ph-H2,6, $^3J_{H,H3(5)}$=3.3 Hz); 7.21 (d; 1H, Fu-H3, $^3J_{H,H3(5)}$=3.3 Hz); 7.07 (d; 1H, ThiazFu-H3, $^2J_{H,H4}$=3.3 Hz); 6.91 (d; 1H, ThiazFu-H4, $^2J_{H,H3}$=3.3 Hz); 6.71 (m; 1H, Fu-H4); 2.98 (s; 3H, —N—CH$_3$)

$^{13}$C-NMR: (DMSO-d$_6$) δ (ppm)=165.54 (s; C=O); 161.63 (d; Ph-C4, $^1J_{C,F}$=245.1 Hz); 160.28 (s; Thiaz-C2); 156.19 (s; Th-C4); 152.02 (s; ThiazFu-C5); 147.90 (s; ThiazFu-C2); 146.93 (s; Fu-C2); 144.50 (d; Fu-C5); 138.77 (s; Th-C7a); 137.46 (s; Th-C4a*, s; Thiaz-C4*); 134.30 (s; Th-C6); 126.50 (s; Ph-C1); 125.72 (dd; Ph-C2,6, $^3J_{C,F}$=7.9 Hz); 117.59 (d; Th-C7); 115.92 (dd; Ph-C3,5, $^2J_{C,F}$=22.1 Hz); 112.91 (d; Fu-C3); 110.24 (d; Th-C3); 109.37 (s; Fu-C4*, d; ThiazFu-C3*); 107.67 (d; ThiazFu-C4*, d; Thiaz-C5*); 39.08 (q; —N—CH$_3$)

EXAMPLE 8

N-[4-(2-Benzo[b]furanyl)-2-thiazolyl]-6-chloro-4-hydroxy-2-methyl-2H-thieno[2,3-e]-1,2-thiazine-3-carboxamide 1,1-dioxide 0.212 g (0.68 mmol) of methyl 6-chloro-4-hydroxy-2-methyl-2H-thieno[2,3-e]-1,2-thiazine-3-carboxylate 1,1-dioxide and 0.154 g (0.71 mmol) of 4-(2-benzo[b]furanyl)-2-thiazolamine are heated to boiling in 3 ml of absolute xylene for 3.5 h. The mixture is then cooled, and the precipitated product is filtered off and digested with a little cold diethyl ether and with hot ethanol.

Yield: 0.240 g of yellow crystals (70.6% of theory)

M.p.: decomposition above 225° C. (EtOH)

TLC: CH$_2$Cl$_2$/MeOH 9:1 Rf: 0.3

$^1$H-NMR: (DMSO-d$_6$) δ (ppm)=7.75–7.56 (m; 2H, Bz-H4,7); 7.66 (s; 1H, Thiaz-H5); 7.65 (s; 1H, Th-H7); 7.4–7.26 (m; 2H, Bz-H5,6); 7.23 (s; Bz-H3); 2.94 (s; 3H, —N—CH$_3$)

$^{13}$C-NMR: (DMSO-d$_6$) δ (ppm)=164.92 (s; C=O); 159.60 (s; Thiaz-C2); 155.28 (s; Th-C4); 154.08 (s; Bz-C2); 150.42 (s; Bz-C7a); 138.06 (s; Th-C4a); 137.23 (s; Th-C7a); 136.05 (s; Thiaz-C4*); 135.86 (s; Th-C6*); 128.24 (s; Bz-C4a); 124.82 (d; Bz-C5); 123.33 (d; Bz-C4); 122.86 (d; Th-C7); 121.53 (d; Bz-C6); 111.00 (d; Bz-C7); 110.59 (d; Thiaz-C5*); 110.13 (s; Th-C3*); 102.99 (d; Bz-C3); 39.19 (q; —N—CH$_3$)

EXAMPLE 9

N-[4-(2-Benzo[b]furanyl)-2-thiazolyl]-6-(2-furanyl)-4-hydroxy-2-methyl-2H-thieno[2,3-e]-1,2-thiazine-3-carboxamide 1,1-dioxide 0.285 g (0.84 mmol) of methyl 6-(2-furanyl)-4-hydroxy-2-methyl-2H-thieno[2,3-e]-1,2-thiazine-3-carboxylate 1,1-dioxide and 0.194 g (0.90 mmol) of 4-(2-benzo[b]furanyl)-2-thiazolamine are heated to boiling in 3 ml of absolute xylene for 5 h. After cooling, the precipitated product is filtered off and digested with a little cold diethyl ether and with hot ethanol.

Yield: 0.340 g of yellow crystals (77.3% of theory)

M.p.: decomposition above 233° C. (EtOH)

TLC: CH$_2$Cl$_2$/MeOH 9:1 Rf: 0.3

$^1$H-NMR: (DMSO-d$_6$) δ (ppm)=7.83 (s; 2H, Th-H7, Fu-H5); 7.7 (s; 1H; Thiaz-H5); 7.77–7.53 (m; 2H, Bz-H4,7); 7.43–7.13 (m; 3H; Bz-H5,6, Fu-H3); 7.24 (s; 1H, Bz-H3); 6.70 (dd; 1H, Fu-H4); 3.00 (s; 3H, —N—CH$_3$)

$^{13}$C-NMR: (DMSO-d$_6$) δ (ppm)=165.35 (s; C=O); 159.00 (s; Thiaz-C2*);155.52 (s; Th-C4); 154.08 (s; Bz-C2); 150.57 (s; Bz-C7a); 146.76 (s; Fu-C2); 144.53 (d; Fu-C5); 139.24 (d; Thiaz-C4*); 139.00 (s; Th-C7a*); 138.75 (s; Th-C4a*); 133.06 (s; Th-C6); 128.25 (s; Bz-C4a); 124.88 (d; Bz-C6); 123.30 (d; Bz-C4); 121.51 (d; Bz-C6); 117.62 (d; Th-C7); 112.91 (d; Fu-C3); 110.99 (d; Bz-C7*); 109.98 (d; Fu-C4*); 109.69 (s; Th-C3); 107.85 (d; Thiaz-C5*); 102.95 (s; Bz-C3); 39.35 (q; —N—CH$_3$)

EXAMPLE 10

N-[4-(2-Benzo[b]furanyl)-2-oxazolyl]-6-chloro-4-hydroxy-2-methyl-2H-thieno-[2,3-e]-1,2-thiazine-3-carboxamide 1,1-dioxide 279 mg (1.39 mmol) of 4-(2-benzo[b]furanyl)-2-oxazolamine and 431 mg (1.39 mmol) of methyl 6-chloro- 4-hydroxy-2-methyl-2H-thieno[2,3-e]-1,2-thiazine-3-carboxylate 1,1-dioxide are heated to boiling in 30 ml of abs. xylene for 25 hours. After cooling, the precipitated orange crystals are filtered off and digested 3 times with cold diethyl ether.

Yield: 240 mg of yellow crystals (36% of theory)

M.p.: 218° C.

$R_F$=0.35 (CHCl$_3$/MeOH=10/1)

$^1$H-NMR: (DMSO-d$_6$) δ (ppm)=8.48 (s, 1H, Thiaz-H7); 7.76 (s, 1H, Bzfu-H3); 7.69 (d, 1H, Bzfu-H4); 7.61 (d, 1H, Bzfu-H7); 7.43–7.22 (m, 2H, Bzfu-H5, H6); 7.18 (s, 1H, Ox-H5); 2.92 (s, 3H, —CH$_3$)

$^{13}$C-NMR: (DMSO-d$_6$) δ (ppm): 164.83 (s, —C=O); 155.66 (s, Ox-C2); 154.04 (s, Ox-C4); 153.35 (s, Thiaz-C3); 147.93 (s, Bzfu-C2); 137.40 (s, Thiaz-C4); 136.19 (s, Thiaz-C4a); 135.63 (s, Thiaz-C7a), 132.91 (d, Bzfu-C3); 131.01 (s, Bzfu-C3a); 128.02 (s, Bzfu-C7a); 124.98 (d, Bzfu-C6); 123.36 (d, Bzfu-C5); 123.00 (d, Thiaz-C7); 121.39 (d, Bzfu-C4); 110.97 (d, Bzfu-C7); 109.95 (s, Thiaz-C6); 103.47 (d, Ox-C5); 39.29 (q, —CH$_3$)

The starting material can be prepared as follows:

4-(2-Benzo[b]furanyl)-2-oxazolamine 5.00 g (25.69 mmol) of 1-(2-benzo[b]furanyl)-2-chloroethanone and 7.71 g (128.45 mmol) of urea are stirred in 20 ml of abs. dimethylformamide at 90° C. for 2.5 hours. The reaction mixture is partitioned between 100 ml of water and 150 ml of ethyl acetate. The organic phase is extracted 3 times with a total of 150 ml of 2N hydrochloric acid. The combined acidic phases are made alkaline with sodium hydroxide pellets and extracted 3 times with a total of 150 ml of ethyl acetate. The combined organic phases are dried over sodium sulphate/active charcoal and filtered, and the solvent is stripped off. The product is isolated by column chromatography. (Mobile phase: trichloromethane/methanol=40/1 50 g of silica gel 60 F$_F$=0.2)

Yield: 390 mg of colourless crystals (7.5% of theory)

M.p.: 215° C. decomposition (acetone)

$R_F$=0.2 (trichloromethane/methanol=40/1)

$^{13}$H-NMR: (DMSO-d$_6$): δ (ppm)=7.89 (s, 1H, Ox-H5); 7.63 (d, 1H, Bzfu-H4); 7.53 (d, 1H, Bzfu-H7); 7.38–7.10 (m, 2H, Bzfu-H5, H6); 6.96 (s, 1H, Bzfu-H3)

$^{13}$C-NMR: (DMSO-d$_6$): δ (ppm): 162.18 (s, Ox-C2); 154.19 (s, Ox-C4); 149.93 (s, Bzfu-C2); 131.54 (s, Bzfu-C3a); 129.00 (d, Bzfu-C3); 128.56 (s, Bzfu-C7a); 124.77 (d, Bzfu-C6); 123.45 (d, Bzfu-C5); 121.32 (d, Bzfu-C4); 111.09 (d, Bzfu-C7); 102.51 (d, Ox-C5)

EXAMPLE 11

N-[4-(2-Benzo[b]furanyl)-2-oxazolyl]-6-2-furanyl)-4-hydroxy-2-methyl-2H-thieno[2,3-e]-thiazine-3-carboxamide 1,1-dioxide 133 mg (0.66 mmol) of 4-(2-benzo[b]furanyl)-2-oxazolamine and 227 mg (0.66 mmol) of methyl 6-(2-furanyl)-4-hydroxy-2-methyl-2H-thieno[2,3-e]-1,2-thiazine-3-carboxylate 1,1-dioxide are heated to boiling in 3 ml of abs. xylene for 5 hours. After the solution has cooled, the precipitated crystals are filtered off and digested 3 times with diethyl ether and twice with hot ethanol.

Yield: 150 mg of yellow crystals (44% of theory)

M.p.: 216° C. (EtOH)

$R_F$=0.35 (trichloromethane/methanol 10/1)

$^1$H-NMR: (DMSO-d$_6$): δ (ppm) : 8.54 (s, 1H, Thiaz-H7); 7.92–7.84 (m, 2H, Ox-H5 and Fu-H5); 7.71 (d, 1H, Bzfu-H4); 7.62 (d, 1H, Bzfu-H7); 7.42–7.23 (m, 3H, Bzfu-H5, H6 and Fu-H3); 7.21 (s, 1H, Bzfu-H3); 6.77–6.68 (m, 1H, Fu-H4); 2.98 (s, 3H, —CH$_3$) $_{13}$C-NMR: (DMSO-d$_6$) δ (ppm): 165.73 (s, —C=O); 156.44 (s, Ox-C2); 154.09 (s, Thiaz-C3); 153.32 (s, Bzfu-C2); 147.99 (s, Fu-C2); 146.78 (s, Ox-C4); 144.71 (d, Fu-C5); 139.45 (Thiaz-C4)*; 139.22 (s, Thiaz-C4a)*; 133.22 (d, Bzfu-C3)*; 132.89 (s, Thiaz-C7a)*; 131.10 (s, Bzfu-C4a); 128.06 (s, Bzfu-C7a); 124.98 (d, Bzfu-C6); 123.37 (d, Bzfu-C5); 121.82 (d, Bzfu-C4); 117.82 (d, Thiaz-C7); 113.00 (d, Fu-C3); 111.01 (d, Fu-C4); 109.87 (d, Bzfu-C7)*; 109.77 (s, Thiaz-C6)*; 103.48 (d, Ox-C5); 39.39 (q, —CH$_3$)

EXAMPLE 12

N-[4-(2-Benzo[b]thienyl)-2-oxazolyl]-6-chloro-4-hydroxy-2-methyl-2H-thieno[2,3e]-thiazine-3-carboxamide 1,1-dioxide 214 mg (0.99 mmol) of 4-(2-benzo[b]thienyl)-2-oxazolamine and 306 mg (0.99 mmol) of methyl 6-chloro-4-hydroxy-2-methyl-2H-thieno[2,3-e]-1,2-thiazine-3-carboxylate 1,1-dioxide are heated to boiling in 19 ml of abs. xylene for 5 hours. After the solution has cooled, the precipitated crystals are filtered off, recrystallized from acetone/active charcoal, filtered and digested twice with hot acetonitrile.

Yield: 104 mg of yellow crystals (21% of theory)

M.p.: 211°–212° C. (acetonitrile)

$R_F$=0.3 (trichloromethane/methanol 10/1)

$^1$H-NMR: (DMSO-d$_6$): δ (ppm)=8.50 (s, 1H, Thiaz-H7); 8.05 (d, 1H, Bzth-H4); 7.87 (d, 1H, Bzth-H7); 7.78 (s, 1H, Bzth-H3); 7.72 (s, 1H, Ox-H5); 7.55–7.28 (m, 2H Bzth-H5, H6)

$_{13}$C-NMR: (DMSO-d$_6$): δ (ppm): 165.09 (s, —C=O); 155.82 (s, Ox-C2); 153.01 (s, Thiaz-C3); 139.73 (s, Ox-C4); 138.45 (s, Thiaz-C4a); 137.50 (s, Thiaz-C7a); 136.14 (s, Bzth-C2); 135.36 (s, Thiaz-C4); 134.13 (s, Bzth-C3a); 133.10 (s, Bzth-C7a); 132.36 (d, Bzth-C3); 124.81 (d, Bzth-C6); 124.75 (d, Ox-C5); 123.74 (d, Bzth-C4); 123.12 (d, Bzth-C5); 122.50 (d, Thiaz-C7), 120.55 (d, Bzth-C7); 110.01 (s, Thiaz-C6); 39.34 (q, —CH$_3$)

The starting material can be prepared as follows:

4-(2-Benzo[b]thienyl)-2-oxazolamine 4.50 g (21.36 mmol) of 1-(2-benzo[b]thienyl)-2-chloroethanone and 6.41 g (106.8 mmol) of urea are stirred in 20 ml of abs. dimethylformamide at 90° C. for 7 hours. The reaction mixture is partitioned between 100 ml of water and 150 ml of ethyl acetate. The organic phase is extracted 3 times with a total of 150 ml of 2N hydrochloric acid. The combined acidic phases are made alkaline with sodium hydroxide pellets and extracted 3 times with a total of 150 ml of ethyl acetate. The combined organic phases are dried over sodium sulphate/active charcoal and filtered, and the solvent is stripped off. The product is isolated by column chromatography. (Mobile phase: trichloromethane/methanol=40/1 50 g of silica gel 60 F$_F$=0.2)

Yield: 560 mg of colourless crystals (12% of theory)

M.p.: 215° C. decomposition (acetone)

$R_F$=0.2 (trichloromethane/methanol=40/1)

$^1$H-NMR: (DMSO-d$_6$) δ (ppm) : 7.95 (s, 1H, Bzth-H3); 7.93 (d, 1H, Bzth-H4); 7.79 (d, 1H, Bzfu-H7); 7.58 (s, 1H, Ox-H5) 7.40–7.25 (m, 2H, Bzfu-H5,H6)

$^{13}$C-NMR: (DMSO-d$_6$) δ (ppm): 161.54 (s, Ox-C2); 139.88 (s, Ox-C4); 138.14 (s, Bzth-C2); 135.14 (s, Bzth- C3a); 134.20 (d, Bzth-C7a); 127.76 (s, Bzth-C3); 124.54 (d, Bzth-C6); 124.17 (d, Ox-C5); 123.29 (d, Bzth-C4); 122.30 (d, Bzth-C5); 118.89 (d, Bzth-C7)

EXAMPLE 13

N-[4-(2-Benzo[b]thienyl)-2-oxazolyl]-6-(2-furanyl)-4-hydroxy-2-methyl-2H-thieno[2,3-e]-1,2-thiazine-3-carboxamide 1,1-dioxide 306 mg (1.41 mmol) of 4-(2-benzo[b]thienyl)-2-oxazolamine and 482 mg (1.41 mmol) of methyl 6-(2-furanyl)-4-hydroxy-2-methyl-2H-thieno[2,3-e]-1,2-thiazine-3-carboxylate 1,1-dioxide are heated to boiling in 7 ml of abs. xylene for 24 hours. After the solution has cooled, the precipitated orange crystals are filtered off and digested with cold diethyl ether.

Yield: 150 mg of yellow crystals (19% of theory)

M.p.: 225° C. (decomposition, diethyl ether)

$R_F$=0.35 (trichloromethane/methanol 10/1)

$^1$H-NMR: (DMSO-$d_6$): δ (ppm): 8.42 (s, 1H, Thiaz-H7); 7.99 (d, 1H, Bzth-H4); 7.91–7.78 (m, 2H, Bzth-H7 and Ox-H5); 7.71–7.65 (m, 2H, Bzth-H3 and Fu-H3); 7.50–7.27 (m, 2H, Bzth-H5,H6); 7.12 (d, 1H, Fu-H5); 6.72–6.68 (m, 1H, Fu-H4); 2.91 (s, 3H, —CH$_3$)

$^{13}$C-NMR: (DMSO-$d_6$): δ (ppm): 163.35 (s, —C=O); 159.95 (s, Ox-C2); 154–03 (s, Thiaz-C3); 147.21 (s, 2C, Fu-C2 u. Thiaz-C6); 144.17 (d, Fu-C5); 139.79 (s, Ox-C4); 138.39 (s, 2C, Thiaz-C3a, C7a)*; 138.14 (s, Bzth-C2)*; 137.72 (s, Thiaz-C4)*; 134.17 (s, Thiaz-C7a); 133.75 (s, Bzth-C7a); 131.36 (d, Bzth-C3); 124.73 (d, Bzth-C6); 124.59 (d, Ox-C5); 123.63 (d, Bzth-C4); 122.47 (d, Bzth-C5); 120.16 (d, Thiaz-C7); 117.43 (d, Bzth-C7); 112.78 (d, Fu-C3); 108.87 (d, Fu-C4); 39.33 (q, —CH$_3$)

EXAMPLE 14

4-Hydroxy-2-methyl-6-phenyl-N-(2-pyridinyl)-2H-thieno-[2,3-e]-1,2-thiazine-3-carboxamide 1,1-dioxide 900 mg (2.56 mmol) of methyl 4-hydroxy-2-methyl-6-phenyl-2H-thieno[2,3-e]-1,2-thiazine-3-carboxylate 1,1-dioxide and 482 mg (5.12 mmol) of 2-pyridinamine are heated to boiling in 18 ml of absolute xylene for 6½ hours. The cooled reaction mixture is diluted with 20 ml of diethyl ether, and the precipitate is filtered off and digested with 15 ml of cold diethyl ether. The crude product is then recrystallized from dimethyl sulphoxide/active charcoal.

Yield: 495 mg of yellow crystals (47% of theory)

TLC: solvent CH$_2$Cl$_2$:MeOH=40:1; 0.35

M.p.: 235°–238° C. (decomposition, methanol)

Elemental microanalysis:

$^1$H-NMR: (DMSO-$d_6$) d(ppm): 8.33 (dd, 1H, Py-H6); 8.17 (ddd, 1H, Py-H4); 7.88 (s, 1H, TT-H7); 7.87–7.78 (m, 2H, Bz-H2,6); 7.73 (d, 1H, PyH3); 7.55–7.37 (m, 3H, Bz-H3,4,5); 7.31 (dd, 1H, Py-H5); 2.93 (s, 3H, CH$_3$)

$^{13}$C-NMR: (CF$_3$COOD) d(ppm): 172.6; 162.8; 159.0; 151.3; 151.1; 143.3; 140.6; 134.8; 134.6; 133.9; 132.8; 129.6; 125.0; 122.3; 120.4; 112.2; 43.0

The starting material can be prepared as follows:

Methyl 3-Chlorosulphonyl-5-phenyl-2-thiophenecarboxylate 8.61 g (125 mmol) of sodium nitrite in 15 ml of water are introduced under the surface of the liquid into a suspension of 30.24 g (112 mmol) of methyl 3-amino-5-phenyl-2-thiophenecarboxylate hydrochloride in 175 ml of concentrated hydrochloric acid at −3° C. over the course of 1½ hours, and the mixture is stirred for 2 hours. This solution is poured into a mixture of 790 ml of saturated sulphurdioxide solution in glacial acetic acid (~40% strength) and 51 ml of a saturated aqueous copper(II) chloride solution, and the mixture is stirred at room temperature for 2 hours. The reaction mixture is poured into 1.3 l of ice-water and extracted with 700 ml and twice with 350 ml of dichloromethane each time. The organic phase is washed four times with 700 ml of water each time, dried over Na$_2$SO$_4$/active charcoal and filtered, and the solvent is stripped off. The resulting product is recrystallized from toluene/active charcoal.

Yield: 29.96 g of pale beige crystals (84% of theory)

TLC: solvent Bz:Et$_2$O=10:1; 0.75

M.p.: 152°–154° C. (toluene)

$^1$H-NMR: (CDCl$_3$) d(ppm): 7.80 (s, 1H, Th-H4); 7.67°–7.58 (m, 2H, Bz-H2,6); 7.52–7.41 (m, 3H, Bz-H3,4, 5); 4.01 (s, 3H, CH$_3$)

$^{13}$C-NMR: (DMSO-$d_6$) d(ppm): 161.1; 152.9; 145.3; 132.5; 129.6; 129.3; 127.1; 126.9; 126.1; 52.6

Methyl 3-[N-(methoxycarbonylmethyl)sulphamoyl]-5-phenyl-2-thiophenecarboxylate 31.31 g (98.8 mmol) of methyl 3-chlorosulphonyl-5-phenyl-2-thiophenecarboxylate, 13.65 g (109 mmol) of glycine methyl ester hydrochloride, 15.03 g (109 mmol) of dry potassium carbonate and 160 ml of absolute dichloromethane and 50 ml of absolute methanol are stirred together at 30° C. for 3 hours. A further 2.73 g (21.7 mmol) of glycine methyl ester hydrochloride and 3.01 g (21.7 mmol) of dry potassium carbonate are added, and the conditions are maintained for a further hour. After the solvent has been stripped off, the residue is suspended in 500 ml of ice-water, and the precipitate is filtered off and digested four times with 100 ml of cold water each time. The resulting crude product is recrystallized from acetone/active charcoal. Yield: 30.3 g of colourless crystals (83% of theory)

TLC: solvent Bz:Et$_2$O=5:1; 0.25

M.p.: 151°–152° C. (acetone)

$^1$H-NMR: (DMSO-$d_6$) d(ppm): 7.95–7.72 (m, 4H, Th-H4, Bz-H2,6, NH); 7.62–7.40 (m, 3H, Bz-H3,4,5); 3.98 (d, 2H, CH$_2$); 3.91 (s, 3H, Th-COOCH$_3$); 3.55 (s, 3H, CH$_2$—COOCH$_3$)

$^{13}$C-NMR: (DMSO-$d_6$) d(ppm): 169.6; 159.9; 147.3; 145.4; 131.2; 129.7; 129.4; 129.0; 126.0; 125.7; 53.1; 51.8; 44.2

Methyl 4-hydroxy-6-phenyl-2H-thieno[2,3-e]-1,2-thiazine-3-carboxylate 1,1-dioxide 20.89 g (56.5 mmol) of methyl 3-[N-(methoxycarbonylmethyl)sulphamoyl]-5-phenyl-2-thiophenecarboxylate in 210 ml of absolute tetrahydrofuran are added dropwise to 13.96 g (124 mmol) of potassium tert-butanolate in 170 ml of absolute tetrahydrofuran at −5° to 0° C. with vigorous mechanical stirring, and the mixture is then stirred for one hour.

After addition of 840 ml of ice-cold 2N hydrochloric acid, the precipitate is filtered off and digested twice with 100 ml of cold water each time and twice with 100 ml of cold methanol each time. The resulting crude product is recrystallized from chlorobenzene/active charcoal.

Yield: 12.42 g of yellow crystals (65% of theory)
TLC: solvent $CH_2Cl_2$:MeOH=40:1; 0.4
M.p.: 219°–223° C. (decomposition, chlorobenzene)
$^1$H-NMR: (DMSO-$d_6$) d(ppm): 8.05 (s, 1H, TT-H7); 7.93–7.80 (m, 2H, Bz-H2,6); 7.58–7.39 (m, 3H, Bz-H3,4,5); 3.90 (s, 3H, C$\underline{H}_3$)
$^{13}$C-NMR: (DMSO-$d_6$) d(ppm): 166.9; 149.9; 149.7; 140.6; 133.0; 131.6; 129.7; 129.4; 126.6; 126.1; 117.7; 105.0; 52.7

Methyl 4-hydroxy-2-methyl-6-phenyl-2H-thieno[2,3-e]-1,2-thiazine-3-carboxylate 1,1-dioxide 9.68 g (28.7 mmol) of methyl 4-hydroxy-6-phenyl-2H-thieno[2,3-e]-1,2-thiazine-3-carboxylate 1,1-dioxide in 33 ml of absolute N,N-dimethylformamide are added dropwise to a suspension of 0.758 g (31.6 mmol) of sodium hydride in 16 ml of absolute N,N-dimethylformamide at 10° C., and the mixture is stirred for one hour. 4.87 g (34.4 mmol) of iodomethane are added to the resulting solution, and the mixture is stirred at room temperature for 20 hours. After addition of 245 ml of ice-cold 2N hydrochloric acid, the resulting precipitate is filtered off and digested twice with 50 ml of cold water each time and once with 30 ml of cold acetone. The resulting crude product is recrystallized from toluene/active charcoal and digested twice with 50 ml of cold petroleum ether each time.

Yield: 8.71 g of yellow crystals (86% of theory)
TLC: solvent Bz:MeOH=10:1; 0.7
M.p.: 204°–211° C. (decomposition, toluene)
$^1$H-NMR: (DMSO-$d_6$) d(ppm): 8.05 (s, 1H, TT-H7); 7.95–7.79 (m, 2H, Bz-H2,6); 7.58–7.38 (m, 3H, Bz-H3,4,5); 3.90 (s, 3H, OC$\underline{H}_3$); 2.96 (s, 3H, NC$\underline{H}_3$)
$^{13}$C-NMR: (DMSO-$d_6$) d(ppm): 167.2; 153.6; 151.2; 139.6; 131.5; 129.8; 129.4; 129.4; 126.2; 119.0; 109.2; 52.7; 38.4

EXAMPLE 15

4-Hydroxy-2-methyl-N-(2-pyridinyl)-6-(2-thienyl)-2H-thieno[2,3-e]-1,2-thiazine-3-carboxamide 1,1-dioxide 1.20 g (3.36 mmol) of methyl 4-hydroxy-2-methyl-6-(2-thienyl)-2H-thieno[2,3-e]-1,2-thiazine-3-carboxylate 1,1-dioxide and 632 mg (6.71 mmol) of 2-pyridinamine are heated to boiling in 24 ml of absolute xylene for 7 hours. The cooled reaction mixture is diluted with 25 ml of diethyl ether, and the resulting precipitate is filtered off and digested with 15 ml of cold diethyl ether. The crude product is recrystallized from dimethyl sulphoxide/active charcoal and digested twice with 2 ml of cold acetone each time.

Yield: 679 mg of orange crystals (48% of theory)
TLC: solvent $CH_2Cl_2$:MeOH=40:1; 0.3
M.p.: 239°–242° C. (decomposition, DMSO)
$^1$H-NMR: (DMSO-$d_6$) d(ppm): 8.32 (dd, 1H, Py-H6); 8.17 (ddd, 1H, Py-H4); 7.77–7.56 (m, 4H, Py-H3, TT-H7, Th-H3,5); 7.31 (dd, Py-H5); 7.16 (dd, Th-H4); 2.93 (s, 3H, C$\underline{H}_3$)
$^{13}$C-NMR: (CF$_3$COOD) d(ppm): 172.9; 163.5; 153.3; 151.6; 142.8; 140.8; 137.2; 137.1; 133.9; 132.2; 132.1; 131.1; 125.3; 122.1; 120.5; 111.9; 43.3

The starting material can be prepared as follows:

2-Cyano-1-(2-thienyl)ethenyl 4-methylbenzenesulphonate 49.70 g (261 mmol) of p-toluenesulphonyl chloride in 75 ml of absolute dichloromethane are added dropwise to 37.54 g (248 mmol) of b-oxo-2-thiophenepropanenitrile and 35.16 g (348 mmol) of N-methylmorpholine in 75 ml of absolute dichloromethane at 10° to 15° C., and the mixture is stirred for one hour. The solvent is stripped off, the residue is partitioned between 800 ml of ethyl acetate and 300 ml of 0.5N hydrochloric acid and filtered through Hyflo, and the aqueous phase is then extracted with 500 ml of ethyl acetate. The combined extracts are dried over Na$_2$SO$_4$/active charcoal and filtered, and the extractant is removed by distillation. The resulting solid is recrystallized from toluene/active charcoal.

Yield: 40.55 g of pale yellow crystals (53% of theory)
TLC: solvent Bz:Et$_2$O=10:1; 0.6
M.p.: 102°–104° C. (toluene)
$^1$H-NMR: (DMSO-$d_6$) d(ppm): 7.95–7.80 (m, 3H, Bz-H2,6, Th-H5); 7.57–7.42 (m, 3H, Bz-H3,5, Th-H3); 7.15 (dd, 1H, Th-H4); 6.50 (s, 1H, C$\underline{H}$—CN); 2.45 (s, 3H, C$\underline{H}_3$)
$^{13}$C-NMR: (DMSO-$d_6$) d(ppm): 155.1; 146.7; 134.0; 132.5; 131.4; 130.9; 130.3; 128.6; 128.3; 114.6; 88.3; 21.2

Methyl 3-amino-5-(2-thienyl)-2-thiophenecarboxylate 13.06 g (123 mmol) of methyl thioglycolate are added to 6.65 g (123 mmol) of sodium methanolate in 350 ml of absolute methanol at 15°–20° C., and the mixture is stirred at room temperature for 20 minutes. Subsequently 35.79 g (117 mmol) of 2-cyano-1-(2-thienyl)ethenyl 4-methylbenzenesulphonate are added in one portion, and the mixture is stirred for one hour. After the solvent has been stripped off, the residue is partitioned between 400 ml of water and 300 ml of diethyl ether, a further extraction is carried out with 200 ml of dichloromethane, and the organic phase is dried over Na$_2$SO$_4$/active charcoal and filtered, and the solvent is removed by distillation. The crude product is recrystallized from toluene/active charcoal.

Yield: 23.14 g of yellow crystals (82% of theory)
TLC: solvent Bz:Et$_2$O=5:1; 0.4
M.p.: 103°–106° C. (toluene) $^1$H-NMR: (CDCl$_3$) d(ppm): 7.35–7.23 (m, 2H, ThB-H3,5); 7.03 (dd, 1H, ThB-H4); 6.66 (s, 1H, ThA-H4); 5.48 (S$_{broad}$, 2H, N$\underline{H}_2$); 3.87 (S, 3H, C$\underline{H}_3$)
$^{13}$C-NMR: (CDCl$_3$) d(ppm): 164.7; 154.0; 142.0; 136.4; 127.9; 126.0; 125.1; 115.5; 99.2; 51.1

Methyl 3-chlorosulphonyl-5-(2-thienyl)-3-thiophenecarboxylate 7.86 g (114 mmol) of sodium nitrite in 12 ml of water are introduced under the surface of the liquid into a suspension of 23.72 g (99.1 mmol) of methyl 3-amino-5-(2-thienyl)-2-thiophenecarboxylate in 155 ml of concentrated hydrochloric acid at −10° to −3° C. over the course of half an hour, and the mixture is stirred for one hour. This solution is poured into a mixture of 525 ml of saturated sulphur dioxide solution in glacial acetic acid (~40% strength) and 34 ml of a saturated aqueous copper(II) chloride solution and stirred at 30° C. for 2 hours. The reaction mixture is poured into 1l of ice-water and extracted three times with 300 ml of dichloromethane each time. The organic phase is washed four times with 300 ml of water each time, dried over Na$_2$SO$_4$/active charcoal and filtered, and the solvent is stripped off. The resulting crude product is recrystallized from acetonitrile/active charcoal.

Yield: 26.63 g of brown crystals (83% of theory)
TLC: solvent Bz:Et$_2$O=10:1; 0.8

M.p.: 164°–167° C. (acetonitrile)

$^1$H-NMR: (DMSO-d$_6$) d(ppm): 7.60 (dd, 1H, ThB-H5); 7.44 (dd, 1H, ThB-H3); 7.37 (s, 1H, ThA-H4); 7.11 (dd, 1H, ThB-H4); 3.75 (s, 3H, CH$_3$)

$^{13}$C-NMR: (DMSO-d$_6$) d(ppm): 160.9; 153.0; 139.0; 135.2; 129.2; 127.9; 127.0; 126.5; 126.2; 52.7

Methyl 3-[N-(methoxycarbonylmethyl)sulphamoyl]-5-(2-thienyl)-3-thiophenecarboxylate 23.75 g (73.6 mmol) of methyl 3-chlorosulphonyl-5-(2-thienyl)-3-thiophenecarboxylate, 10.16 g (80.9 mmol) of glycine methyl ester hydrochloride, 11.19 g (80.9 mmol) of dry potassium carbonate and 120 ml of absolute dichloromethane and 40 ml of absolute methanol are heated to boiling together for one hour. A further 10.16 g (80.9 mmol) of glycine methyl ester hydrochloride and 11.19 g (80.9 mmol) of dry potassium carbonate are added, and the conditions are then maintained for one hour. After the solvent has been stripped off, the residue is suspended in 450 ml of ice-water, and the crude product is filtered off and digested four times with 100 ml of cold water each time and recrystallized from toluene/active charcoal.

Yield: 23.70 g of pale beige crystals (86% of theory)

TLC: solvent Bz:Et$_2$O=10:1; 0.35

M.P.: 124°–126° C. (toluene)

$^1$H-NMR: (CDCl$_3$) d(ppm): 7.57 (s, 1H, ThA-H4); 7.39 (dd, 1H, ThB-H5); 7.32 (dd, 1H, ThB-H3); 7.08 (dd, 1H, ThB-H4); 6.91 (t, 1H, NH); 3.99 (s, 3H, Th-COOCH$_3$); 3.96 (d, 2H, CH$_2$); 3.62 (s, 3H, CH$_2$—COOCH$_2$)

$^{13}$C-NMR: (CDCl$_3$) d(ppm): 168.9; 160.7; 145.0; 142.0; 134.2; 128.4; 127.6; 127.5; 126.3; 125.6; 53.1; 52.3; 44.5

Methyl 4-hydroxy-6-(2-thienyl)-2H-thieno[2,3e]-1,2-thiazine-3-carboxylate 1,1-dioxide 24.65 g (65.7 mmol) of methyl 3-[N-(methoxycarbonylmethyl)sulphamoyl]-5-(2-thienyl)-3-thiophenecarboxylate in 250 ml of absolute tetrahydrofuran are added dropwise to 16.95 g (151 mmol) of potassium tertbutanolate in 200 ml of absolute tetrahydrofuran at −15° C. with vigorous mechanical stirring, and the mixture is stirred for one hour. After addition of 900 ml of ice-cold 2N hydrochloric acid, the precipitate is filtered off and digested with 100 ml of cold water and twice with 50 ml of cold methanol each time. This crude product is recrystallized from acetonitrile/active charcoal.

Yield: 17.70 g of yellow crystals (79% of theory)

TLC: solvent CH$_2$Cl$_2$:MeOH=40:1; 0.4

M.p.: 202°–205° C. (decomposition, acetonitrile)

$^1$H-NMR: (DMSO-d$_6$) d(ppm): 7.80 (s, 1H, TT-H7); 7.71 (d, 1H, Th-H5); 7.66 (d, 1H, Th-H3); 7.18 (dd, 1H, Th-H4); 3.89 (s, 3H, CH$_3$)

$^{13}$C-NMR: (DMSO-d$_6$) d(ppm): 166.8; 149.5; 143.1; 140.4; 134.1; 132.2; 128.8; 128.4; 127.2; 117.4; 105.0; 52.7

Methyl 4-hydroxy-2-methyl-6-(2-thienyl)-2H-thieno[2,3e]-2-thiazine-3-carboxylate 1,1-dioxide 15.28 g (44.5 mmol) of methyl 4-hydroxy-6-(2-thienyl)-2H-thieno[2,3-e]-1,2-thiazine-3-carboxylate 1,1-dioxide in 52 ml of absolute N,N-dimethylformamide are added dropwise to a suspension of 1.17 g (48.9 mmol) of sodium hydride in 65 ml of absolute N,N-dimethylformamide at 10° C., and the mixture is stirred for one hour. 7.58 g (53.4 mmol) of iodomethane are added to the resulting solution, and the mixture is stirred at room temperature for 20 hours. It is hydrolyzed with 600 ml of ice-cold 2N hydrochloric acid, and the resulting precipitate is filtered off and digested twice with 90 ml of cold water each time and once with 30 ml of cold acetone. The resulting crude product is recrystallized from dioxane/active charcoal.

Yield: 13.03 g of yellow crystals (82% of theory)

TLC: solvent Bz:MeOH=10:1; 0.7

M.p.: 212°–218° C. (decomposition, dioxane)

$^1$H-NMR: (DMSO-d$_6$) d(ppm): 7.84 (s, 1H, TT-H7); 7.73 (d, 1H, Th-H5); 7.68 (d, 1H, Th-H3); 7.19 (dd, 1H, Th-H4); 3.90 (s, 3H, OCH$_3$); 2.96 (s, 3H, NCH$_3$)

$^{13}$C-NMR: (DMSO-d$_6$) d(ppm): 167.0; 153.3; 144.3; 139.4; 133.8; 131.5; 128.9; 128.8; 127.5; 118.6; 109.2; 52.7; 38.4

EXAMPLE 16

6-(2-Furyl)-4-hydroxy-2-methyl-N-(2-pyridinyl)-2H-thieno[2,3-e]-1,2-thiazine-3-carboxamide 1,1-dioxide 1.86 g (5.44 mmol) of methyl 6-(2-furyl)-4-hydroxy-2-methyl-2H-thieno[2,3-e]-1,2-thiazine-3-carboxylate 1,1-dioxide and 1.02 g (10.9 mmol) of 2-pyridinamine are heated to boiling in 37 ml of absolute xylene for 4½ hours. The cooled reaction mixture is diluted with 50 ml of diethyl ether, and the resulting precipitate is filtered off and digested with 20 ml of cold diethyl ether. The crude product is recrystallized from dimethyl sulphoxide/active charcoal.

Yield: 1.24 g of yellow crystals (57% of theory)

TLC: solvent CH$_2$Cl$_2$:MeOH=40:1; 0.3

M.p.: 231°–234° C. (decomposition, DMSO)

$^1$H-NMR: (DMSO-d$_6$) d(ppm): 8.32 (d, 1H, Py-H6); 8.17 (dd, 1H, Py-H4); 7.82 (d, 1H, Fu-H5); 7.74 (d, 1H, Py-H3); 7.72 (s, 1H, TT-H7); 7.30 (dd, 1H, Py-H5); 7.15 (d, 1H, Fu-H3); 6.68 (dd, 1H, Fu-B4); 2.93 (s, 3B, CH$_3$)

$^{13}$C-NMR: (CF$_3$COOD) d(ppm): 172.4; 162.7; 151.1; 151.0; 150.0; 148.0; 147.0; 143.5; 140.6; 133.1; 124.8; 120.8; 120.3; 115.9; 113.6; 112.1; 42.9

The starting material can be prepared as follows:

2-Cyano-1-(2-furyl)ethenyl 4-methylbenzenesulphonate 67.78 g (356 mmol) of p-toluenesulphonyl chloride in 100 ml of absolute dichloromethane are added dropwise to 45.75 g (339 mmol) of b-oxo-2-furanpropanenitrile and 47.95 g (474 mmol) of N-methylmorpholine in 100 ml of absolute dichloromethane at −5° to 0° C., and the mixture is stirred for one hour. The solvent is stripped off, the residue is partitioned between 500 ml of ethyl acetate and 400 ml of 1N hydrochloric acid and the aqueous phase is extracted with 6×150 ml of ethyl acetate. The combined extracts are dried over Na$_2$SO$_4$/active charcoal and filtered, and the extractant is removed by distillation. The resulting solid is recrystallized from toluene/active charcoal.

Yield: 92.48 g of colourless crystals (94% of theory)

TLC: solvent Bz:Et$_2$O=10:1; 0.65

M.p.: 109°–111° C. (toluene)

$^1$H-NMR: (DMSO-d$_6$) d(ppm): 8.00–7.85 (m, 3H, Bz-H2, 6, Fu-H5); 7.60–7.48 (m, 2B, Bz-H3,5) 6.74 (dd, 1H, Fu-H3*); 6.57 (dd, 1H, Fu-H4*); 6.33 (s, 1H, CH—CN); 2.45 (s, 3H, CH$_3$)

$^{13}$C-NMR: (DMSO-d$_6$) d(ppm): 150.2; 147.7; 146.8; 145.4; 131.1; 130.4; 128.4; 115.9; 114.4; 113.1; 87.3; 21.2

Methyl 3-amino-5-(2-furyl)-2-thiophenecarboxylate hydrochloride 32.75 g (309 mmol) of methyl thioglycolate are added to 16.75 g (309 mmol) of sodium methanolate in 750 ml of absolute methanol at 15°–20° C., and the mixture is stirred at room temperature for 20 minutes. Subsequently 74.38 g (257 mmol) of 2-cyano-1-(2-furyl)ethenyl 4-methylbenzenesulphonate are added in one portion, and the mixture is stirred for a further 2½ hours. After the solvent has been stripped off, the residue is partitioned between 500 ml of water and 400 ml of diethyl ether, extraction is carried out once more with 200 ml of diethyl ether, and the organic phase is dried over $Na_2SO_4$/active charcoal, filtered and concentrated to 400 ml. Then, dry hydrogen chloride is passed in while cooling in ice and stirring vigorously for one hour, the mixture is cooled to –20° C., and the precipitated hydrochloride is filtered off and digested with 2×100 ml of dry diethyl ether.

Yield: 37.74 g of colourless crystals (57% of theory)

TLC (amine): solvent $Bz:Et_2O=5:1$; 0.4

M.p.: 134°–136° C. (ether)

$^1$H-NMR: (DMSO-$d_6$) d(ppm): 7.79 (dd, 1H, Fu-H5); 7.46 ($S_{broad}$, 3H, N$H_3$Cl); 6.90 (dd, 1H, Fu-H3); 6.87 (S, 1H, Th-H4); 6.62 (dd, 1H, Fu-H4); 3.72 (S, 3H, C$H_3$)

$^{13}$C-NMR: (DMSO-$d_6$) d(ppm): 164.0; 154.2; 148.0; 144.1; 136.9, 115.3; 112.7; 108.6; 97.5, 51.3

Methyl 3-chlorosulphonyl-5-(2-furyl)-2-thiophenecarboxylate 11.29 g (164 mmol) of sodium nitrite in 16 ml of water are introduced under the surface of the liquid into a suspension of 35.42 g (136 mmol) of methyl 3-amino-5-(2-furyl)-2-thiophenecarboxylate hydrochloride in 215 ml of concentrated hydrochloric acid at –12° C. over the course of half an hour, and the mixture is stirred for one hour. This solution is poured into a mixture of 725 ml of saturated sulphur dioxide solution in glacial acetic acid (~40% strength) and 47 ml of a saturated aqueous copper(II) chloride solution, heated to 30° C. and stirred for 2 hours. The reaction mixture is poured into 2 l of ice-water, and the resulting precipitate is filtered off and digested three times with 300 ml of cold water each time. The solid is partitioned between 400 ml of water and 300 ml of dichloromethane, and extraction is carried out three times more with 200 ml of dichloromethane each time. The organic phase is dried over $Na_2SO_4$/active charcoal and filtered, and the solvent is stripped off.

Yield: 38.46 g of brown crystals (92% of theory)

TLC: solvent $Bz:Et_2O=10:1$; 0.7

M.p.: 133°–136° C. (decomposition)

$^1$H-NMR: (CDCl$_3$) d(ppm): 7.68 (s, 1H, Th-H4); 7.51 (dd, 1H, Fu-H5); 6.77 (dd, 1H, Fu-H3); 6.53 (dd, 1H, Fu-H4); 3.99 (s, 3H, C$H_3$)

$^{13}$C-NMR: (CDCl$_3$) d(ppm): 158.7; 146.1; 144.4; 144.1; 137.5; 131.5; 123.3; 112.5; 109.4; 53.1

Methyl 5-(2-furyl)-3-[N-(methoxycarbonylmethyl)sulphamoyl]-2-thiophenecarboxylate 22.69 g (224 mmol) of triethylamine are added dropwise to a suspension of 30.57 g (99.7 mmol) of methyl 3-chlorosulphonyl-5-(2-furyl)-2-thiophenecarboxylate and 15.64 g (125 mmol) of glycine methyl ester hydrochloride in 255 ml of absolute methanol at 0° C., and the mixture is stirred for one hour. The reaction mixture is poured into 750 ml of ice-cold 2N hydrochloric acid, and the resulting crystals are filtered off and digested three times with 200 ml of ice-cold water each time. The crude product is recrystallized from methanol/active charcoal.

Yield: 29.61 g of brown crystals (83% of theory)

TLC: solvent $Bz: Et_2O=10:1$; 0.3

M.p.: 102°–105° C. (methanol)

$^1$H-NMR: (CDCl$_3$) d(ppm): 7.60 (s, 1H, Th-H4); 7.48 (dd, 1H, Fu-H5); 6.91 (t, 1H, N$H$); 6.73 (dd, 1H, Fu-H3); 6.51 (dd, 1H, Fu-H4); 3.95 (s, 3H, Th-COOC$H_3$); 3.92 (d, 2H, C$H_2$); 3.62 (s, 3H, CH$_2$—COOC$H_3$)

$^{13}$C-NMR: (CDCl$_3$) d(ppm): 168.9; 160.9; 146.8; 145.0; 143.7; 137.6; 127.5; 124.3; 112.3; 108.9; 53.0; 52.3; 44.5

Methyl 6-(2-furyl)-4-hydroxy-2H-thieno[2,3-e]-1,2-thiazine-3-carboxylate 1,1-dioxide 32.11 g (89.3 mmol) of methyl 5-(2-furyl)-3-[N-(methoxycarbonylmethyl)sulphamoyl]-2-thiophenecarboxylate in 330 ml of absolute tetrahydrofuran are added dropwise to 23.06 g (206 mmol) of potassium tert-butanolate in 265 ml of absolute tetrahydrofuran at –10° to –5° C., and the mixture is stirred for half an hour. After addition of 1.2 l of ice-cold 2N hydrochloric acid, the crude product is filtered off and digested three times with 250 ml of cold water each time and once with 100 ml of cold methanol.

Yield: 23.66 g of orange crystals (81% of theory)

TLC: solvent $CH_2Cl_2:MeOH=40:1$; 0.4

M.p.: 215°–222° C. (decomposition, methanol)

$^1$H-NMR: (DMSO-$d_6$) d(ppm): 7.88 (s, 1H, TT-H7); 7.87 (d, 1H, Fu-H5); 7.22 (d, 1H, Fu-H3); 6.70 (dd, 1H, Fu-H4); 3.89 (s, 3H, C$H_3$)

$^{13}$C-NMR: (DMSO-$d_6$) d(ppm): 166.8; 149.7; 146.8; 144.6; 140.4; 138.6; 132.0; 116.2; 112.9; 109.7; 104.9; 52.7

Methyl 6-(2-furyl)-4-hydroxy-2-methyl-2H-thieno[2,3-e]-1,2-thiazine-3-carboxylate 1,1-dioxide 22.81 g (69.7 mmol) of methyl 6-(2-furyl)-4-hydroxy-2H-thieno[2,3-e]-1,2-thiazine-3-carboxylate 1,1-dioxide in 160 ml of absolute DMF are added dropwise to a suspension of 1.84 g (76.7 mmol) of sodium hydride in 40 ml of absolute DMF at –10° C. to –7° C., and the mixture is stirred for one hour. 11.87 g (83.6 mmol) of iodomethane are added to the resulting solution, and the mixture is stirred at room temperature for 20 hours.

After addition of 1 l of ice-cold 2N hydrochloric acid, the resulting precipitate is filtered off and digested twice with 100 ml of cold water each time and once with 70 ml of cold methanol. The crude product is recrystallized from 250 ml of dioxane/active charcoal and digested with 20 ml of cold acetone.

Yield: 19.73 g of yellow crystals (83% of theory)

TLC: solvent $Bz:MeOH=10:1$; 0.65

M.p.: 219°–222° C. (decomposition, dioxane)

$^1$H-NMR: (DMSO-$d_6$) d(ppm): 7.91 (s, 1H, TT-H7); 7.87 (d, 1H, Fu-H5); 7.26 (d, 1H, Fu-H3); 6.71 (dd, 1H, Fu-H4); 3.85 (s, 3H, OC$H_3$); 2.95 (s, 3H, NC$H_3$);

$^{13}$C-NMR: (DMSO-$d_6$) d(ppm): 167.0; 153.5; 146.6; 144.8; 139.8; 139.4; 131.3; 117.5; 113.0; 110.1; 109.1; 52.7; 38.4

EXAMPLE 17

N-[6-(2-Benzo[b]furyl)-2-pyridinyl]-4-hydroxy-2-methyl-6-phenyl-2H-thieno[2,3-e]-1,2-thiazine-3-carboxamide 1,1-dioxide 700 mg (1.99 mmol) of methyl 4-hydroxy-2-methyl-6-phenyl-2H-thieno[2,3-e]-1,2-thiazine-3-carboxylate 1,1- dioxide and 419 mg (1.99 mmol) of 6-(2-benzo[b]furyl)-2-pyridinamine are heated to boiling in 7 ml of absolute xylene for 10 hours. The cooled reaction mixture is diluted with 16 ml of diethyl ether, and the resulting precipitate is filtered off and digested twice with 15 ml of cold diethyl ether each time. This crude product is recrystallized from chloroform/active charcoal.

Yield: 789 mg of yellow crystals (75% of theory)

TLC: solvent PE: EtOH=2:1; 0.3

M.p.: 226°–227° C. (decomposition, chloroform)

$^1$H-NMR: (DMSO-$d_6$) d(ppm): 8.10–7.61 (m, 9H, TT-H7, Bz-H2,6, Py-H3,4,5, BF-H3,4,7); 7.59–7.43 (m, 3H, Bz-H3, 4,5); 7.41 (ddd, 1H, BF-H6); 7.31 (ddd, 1H, BF-H5)

$^{13}$C-NMR: (CF$_3$COOD) d(ppm): 173.4; 162.6; 159.8; 159.4; 151.1; 151.1; 147.4; 143.6; 142.0; 134.5; 134.3; 133.0; 133.0; 131.3; 129.2; 128.7; 126.9; 122.2; 122.2; 120.6; 117.5; 116.2; 115.6; 112.6; 43.3

N-[6-(2-Formyl-phenoxymethyl)-2-pyridyl]-acetamide 20 g (73.8 mmol) of N-acetyl-N-(6-bromomethyl-2-pyridyl)acetamide, 9 g (73.8 mmol) of 2-hydroxybenzaldehyde, 45.9 g (331.3 mmol) of dry potassium carbonate and 0.12 g (7.4 mmol) of potassium iodide are suspended in 200 ml of dimethylformamide and heated at 85° C. for 5 hours. The reaction mixture is cooled and filtered, and the solvent is stripped off. The residue is taken up in 80 ml of dichloromethane, the organic phase is washed twice with 40 ml of 2N aqueous sodium hydroxide solution each time and twice with 40 ml of water each time, dried with sodium sulphate and filtered, and the solvent is stripped off. The crude product is purified by-column chromatography (300 g of silica gel 60; (H$_2$Cl$_2$:EA=2:1).

Yield: 12 g of pale yellow crystals (60% of theory)

TLC: solvent CH$_2$Cl$_2$:EA=2:1; 0.5

M.p.: 169°–171° C. (EtOH)

$^1$H-NMR: (CDCl$_3$) d(ppm): 10.58 (s, 1H, Ph-C$\underline{H}$O); 8.17 (d, 1H, Py-H3); 8.03 (s, 1H, Py-N$\underline{H}$—); 7.86 (d, 1H, Ph-H3); 7.75 (dd, 1H, Py-H4); 7.53 (dd, 1H, Ph-H5); 7.23 (d, 1H, Py-H5); 7.05 (dd, 1H, Ph-H4); 6.98 (d, 1H, Ph-H6); 5.17 (s; 2H, Py-C$\underline{H}_2$—O—); 2.21 (s, 3H, C$\underline{H}_3$—CO—)

$^{13}$C-NMR: (DMSO-$d_6$) d(ppm): 188.6; 169.0; 159.8; 151.0; 138.1; 135.3; 127.7; 124.2; 120.4; 115.9; 112.5; 112.3; 70.0; 23.6

N-[6-(2-Benzo[b]furyl)-2-pyridyl]-acetamide 11g (40.7 mmol) of N-[6-(2-formylphenoxymethyl)-2-pyridyl]acetamide are heated under a nitrogen atmosphere in a sand bath at 300° C. for 20 minutes. The cooled crude product is purified by chromatography (100 g of silica gel 60; CH$_2$Cl$_2$:EA=2:1). The resulting product is used in the next stage without further purification.

Yield: 3.4 g of colourless crystals (33% of theory)

TLC: solvent CH$_2$Cl$_2$:Et$_2$O=2:1; 0.6

M.p.: 191°–193° C. (acetone)

$^1$H-NMR: (CDCl$_3$) d(ppm): 8.26 (s, 1H, Py-N$\underline{H}$—); 8.18 (d, 1H, Py-H3); 7.79 (dd, 1H, Py-H4); 7.62 (d, 2H, BzFu-H4, Py-H5); 7.56 (d, 1H, BzFu-H7); 7.39–7.20 (m, 2H, BzFu-H5, H6); 7.32 (s, 1H, BzFu-H3); 2.21 (s, 3H, C$\underline{H}_3$—CO—)

$^{13}$C-NMR: (CDCl$_3$) d(ppm): 168.8; 155.3; 154.5; 151.3; 147.4; 139.2; 128.6; 125.3; 123.3; 121.6; 115.9; 113.3; 111.6; 104.9; 24.7.

6-(2-Benzo[b]furyl-2-pyridinamine 5.5 g (23.8 mmol) of the crude product obtained previously are suspended in 440 ml (190.4 mmol) of 4% strength aqueous sulphuric acid and heated to boiling for 90 minutes. The mixture is cooled, neutralized with saturated aqueous sodium bicarbonate solution and extracted three times with 200 ml of ethyl acerbate each time. The combined organic phases are washed with 100 ml of water, dried with sodium sulphate and filtered, and the solvent is stripped off. The crude product is recrystallized from 60 ml of ethanol/active charcoal.

Yield: 4.3 g of colourless crystals (86% of theory)

TLC: solvent CH$_2$Cl$_2$:Et$_2$O=2:1; 0.5

M.p.: 151°–154° C. (EtOH)

$^1$H-NMR: (DMSO-$d_6$) d(ppm): 7.70 (d, 1H, BzFu-H4); 7.64 (d, 1H, BzFu-H7); 7.51 (dd, 1H, Py-H4); 7.34 (dd, 1H, BzFu-H5); 7.34 (s, 1H, BzFu-H3); 7.27 (dd, 1H, BzFu-H6); 7.11 (d, 1H, Py-H5); 6.49 (d, 1H, Py-H3); 6.20 (s, 2H, Py-N$\underline{H}_2$)

$^{13}$C-NMR: (DMSO-$d_6$) d(ppm): 159.7; 155.8; 154.3; 146.3; 137.7; 128.5; 124.9; 123.1; 121.5; 111.2; 108.6; 108.0; 103.5.

EXAMPLE 18

N-[6-(2-Benzo[b]furyl)-2-pyridinyl]-4-hydroxy-2-methyl-6-(2-thienyl)-2H-thieno[2,3-e]-1,2-thiazine-3-carboxamide 1,1-dioxide 700 mg (1.96 mmol) of methyl 4-hydroxy-2-methyl-6-(2-thienyl)-2H-thieno[2,3-e]-1,2-thiazine-3-carboxylate 1,1-dioxide and 412 mg (1.96 mmol) of 6-(2-benzo[b]-furyl)-2-pyridinamine are heated to boiling in 7 ml of absolute xylene for 10 hours. The cooled reaction mixture is diluted with 20 ml of diethyl ether, and the resulting precipitate is filtered off and digested twice with 15 ml of cold diethyl ether each time. The crude product is recrystallized from dimethyl sulphoxide/active charcoal.

Yield: 821 mg of yellow crystals (78% of theory)

TLC: solvent PE:EtOH=2:1; 0.3

M.p.: 253°–256° C. (decomposition, DMSO)

$^1$H-NMR: (DMSO-$d_6$) d(ppm): 8.08–7.90 (m, 2H, Py-H4, 5); 7.90–7.58 (m, 7H, Th-H3,5, TT-H7, BF-H3,4,7, Py-H3); 7.41 (ddd, 1H, BF-H6); 7.31 (ddd, 1H, BF-H5); 7.20 (dd, 1H, Th-H4); 3.00 (s, 3H, C$\underline{H}_3$)

$_{13}$C-NMR: (CF$_3$COOD) d(ppm): 173.2; 162.9; 159.6; 152.2; 150.9; 147.4; 143.7; 141.7; 136.9; 133.1; 132.7; 132.2; 132.2; 131.2; 130.7; 128.6; 126.7; 121.7; 121.7; 120.4; 117.6; 116.0; 115.5; 112.4; 43.2

EXAMPLE 19

N-[6-(2-Benzo[b]furyl)-2-pyridinyl]-6-(2-furyl)-4-hydroxy-2-methyl-2H-thieno[2,3e]-1,2-thiazine-3-carboxamide 1,1-dioxide 700 mg (2.05 mmol) of methyl 6-(2-furyl)-4-hydroxy-2-methyl-2H-thieno[2,3-e]-1,2-thiazine-3-carboxylate 1,1-dioxide and 431 mg (2.05 mmol) of 6-(2-benzo[b]-furyl)-2-pyridinamine are heated to boiling in 7 ml of absolute xylene for 9 hours. The cooled reaction mixture is diluted with 20 ml of diethyl ether, and the resulting precipitate is filtered off and digested twice with 15 ml of cold diethyl ether each time. The crude product is recrystallized from dioxane/active charcoal.

Yield: 687 mg of yellow crystals (64% of theory)

TLC: solvent PE:EtOH=2:1; 0.3

M.p.: 242°–244° C. (decomposition, dioxane)

$^1$H-NMR: (DMSO-d$_6$) d(ppm): 8.07–7.60 (m, 8H, Fu-H5, TT-H7, BF-H3,4,7, Py-H3,4,5); 7.41 (ddd, 1H, BF-H6); 7.31 (ddd, 1H, BF-H5); 7.25 (dd, 1H, Fu-H3); 6.72 (dd, 1H, Fu-H4); 3.00 (s, 3H, C$\underline{H}_3$)

$^{13}$C-NMR: (CF$_3$COOD) d(ppm): 172.8; 162.9; 159.3; 150.8; 150.6; 149.7; 147.9; 147.5; 146.6; 143.8; 141.5; 132.9; 132.2; 131.0; 128.3; 126.4; 120.6; 120.2; 117.6; 116.0; 115.4; 115.3; 113.5; 112.4; 42.9

EXAMPLE 20

6-(2Furyl)-4-hydroxy-2-methyl-N-[6-phenyl-2-pyridinyl]-2H-thieno[2,3-e]-1,2-thiazine-3-carboxamide 1,1-dioxide 500 mg (1.46 mmol) of methyl 6-(2-furyl)-4-hydroxy-2-methyl-2H-thieno[2,3-e]-1,2-thiazine-3-carboxylate 1,1-dioxide and 431 mg (1.46 mmol) of 6-phenyl-2-pyridinamine are heated to boiling in 6 ml of absolute xylene for 4 hours. After the reaction mixture has cooled, the precipitate is filtered off and digested twice with 15 ml of cold diethyl ether each time. The crude product is recrystallized from toluene/active charcoal.

Yield: 360 mg of yellow crystals (51% of theory)

TLC: solvent PE: EtOH=2:1; 0.3

M.p.: 210°–213° C. (toluene)

$^1$H-NMR: (DMSO-d$_6$) d(ppm): 8.15–8.05 (m, 2H, Bz-H2, 6); 8.04–7.82 (m, 4H, Thaz-H7, Fu-H5, Py-H3,4); 7.78 (d, 1H, Py-H5); 7.57–7.44 (m, 3H, Bz-H3,4,5); 7.22 (d, 1H, Fu-H3); 6.69 (dd, 1H, Fu-H4)

$^{13}$C-NMR: (DMSO-d$_6$) d(ppm): 166.4; 156.5; 153.7; 150.2; 146.8; 144.6; 140.1; 139.3; 138.9; 136.9; 133.2; 129.6; 128.8; 126.7; 117.8; 116.6; 114.5; 112.9; 110.0; 109.8; 39.6

EXAMPLE 21

N-{6-[(2-Benzo[b]furyl)-methoxy]-2-pyridinyl}-6-(2-furyl)-4-hydroxy-2-methyl-2H-thieno[2,3-e]-1,2-thiazine-3-carboxamide 1,1-dioxide 0.127 g (0.53 mmol) of 6-[(2-benzo[b]furyl)-methoxy]-2-pyridinamine and 0.18 g (0.53 mmol) of methyl 6-(2-furyl)-4-hydroxy-2-methyl-2H-thieno[2,3-e]-1,2-thiazine-3-carboxylate 1,1-dioxide are heated to boiling in 10 ml of abs. xylene for 4 hours. The solvent is stripped off and the crude product is digested three times with 5 ml of hot diethyl ether each time.

Yield: 0.14 g of yellow crystals (48% of theory)

TLC: solvent Bz:Dx:AcOH=10:1:1; 0.8

M.p.: 190°–191° C. (toluene)

$^1$H-NMR: (DMSO-d$_6$) δ (ppm): 7.95 (m, 3H, Fu-H5, TT-H7, BF-H6); 7.69–7.52 (m, 3H, BF-H4,5,7) 7.39–7.14 (m, 3H, Py-H3,4, Fu-H3); 7.08 (s, 1H, BF-H3); 6.76–6.67 (m, 2H, Fu-H4, Py-H5); 5.55 (s, 2H, —OC$\underline{H}_2$); 2.99 (s, 3H, —C$\underline{H}_3$)

$^{13}$C-NMR: (DMSO-d$_6$) δ(ppm): 166.0; 161.1; 154.9; 154.3; 152.9; 147.9; 146.5; 144.6; 141.1; 139.3; 138.7; 132.0; 127.5; 124.6; 122.8; 121.2; 117.7; 112.8; 111.0; 110.3; 109.8; 108.2; 106.7; 106.5; 59.6; 39.4

The amino component can be prepared as follows:

6-[(2-Benzo[b]furyl)methoxy]-2-bromopyridine 9.13 ml (50.7 mmol) of a 30% strength solution of sodium methanolate in abs. methanol are added dropwise to 6.83 g (46.1 mmol) of 2-benzo[b]furanmethanol in 50 ml of abs. methanol. The solvent is stripped off and the residue is stirred together with 10.87 g (45.9 mmol) of 2,6-dibromopyridine in 250 ml of abs. N,N-dimethylformamide at 70°–80° C. for 3 hours. The solvent is stripped off and the residue is taken up in ethyl acetate. The organic phase is washed with 0.5N hydrochloric acid, dried over sodium sulphate and filtered, the solvent is distilled off and the crude product is recrystallized from diethyl ether through active charcoal.

Yield: 7.84 g of colourless crystals (56% of theory)

TLC: solvent PE:Bz=4:1; 0.35

M.p.: 91°–92° C. (diethylether)

$^1$H-NMR (CDCl$_3$): δ(ppm): 7.62–7.51 (m, 2H, BF-H4,7); 7.43 (dd, 1H, Py-H4); 7.37–7.18 (m, 2H, BF-H5,6); 7.10 (d, 1H, H3); 6.84 (s, 1H, BF-H3); 6.76 (d, 1H, Py-H5); 5.80 (s, 2H, —OC$\underline{H}_2$)

$^{13}$C-NMR (CDCl$_3$): δ(ppm): 162.3; 155.1; 152.4; 140.6; 138.2; 127.9; 124.6; 122.8; 121.2; 120.7; 111.3; 109.6; 106.9; 60.7

6-[(2-Benzo[b]furyl)-methoxy]-2-pyridinamine 5.89 ml (14.73 mmol) of a 2.5N solution of butyllithium in n-hexane are added to 4.48 g (14.73 mmol) of 6-[(2-benzo[b]furyl)methoxy]-2-bromopyridine in 70 ml of abs. tetrahydrofuran at −80° C., and the mixture is stirred for 30 minutes. Then 2.13 g (14.73 mmol) of 1-azido-1-phenylethene in 28 ml of abs. tetrahydrofuran are added. After room temperature is reached, 200 ml of 10% strength hydrochloric acid are added, and the mixture is stirred for 20 minutes and adjusted to pH=12 with solid sodium hydroxide. The aqueous phase is exhaustively extracted with ethyl acetate. The organic phase is then extracted with 2N hydrochloric acid, and the aqueous phase is adjusted to pH=12 with solid sodium hydroxide and back-extracted. The combined organic phases are dried over sodium sulphate and filtered, and the solvent is stripped off. The product is isolated by chromatography. (Mobile phase: chloroform; 100 g of silica gel)

Yield: 0.38 g of colourless crystals (11.5% of theory)

TLC: solvent CHCl$_3$; 0.1

M.p.: 82°–83° C. (toluene)

$^1$H-NMR (CDCl$_3$): δ(ppm): 7.60–7.43 (m, 2H, BF-H4,7); 7.36 (dd, 1H, Py-H4); 7.30–7.16 (m, 2H, BF-H5,6); 6.77 (s, 1H, BF-H3); 6.18 (d, 1H, Py-H3); 6.08 (d, 1H, Py-H5); 5.40 (s, 2H, —OC$\underline{H}_2$)

$^{13}$C-NMR (CDCl$_3$): δ(ppm): 162.3; 156.9; 155.0; 153.7; 140.4; 128.1; 124.3; 122.6; 121.0; 111.2; 105.9; 100.1; 99.3; 59.8

EXAMPLE 22

N-{6-[(2Benzo[b]thienyl)-methoxy]-2-pyridyl}-6-(2-furyl)-4-hydroxy-2-methyl-2H-thieno[2,3-e]-1,2-thiazine-3-carboxamide 1,1-dioxide 0.41 g (1.61 mmol) of 6-[(2-benzo[b]thienyl)-methoxy]-2-pyridinamine and 0.5 g (1.46 mmol) of methyl 6-(2-furyl)-4-hydroxy-2-methyl-2H-thieno[2,3-e]-1,2-thiazine-3-carboxylate 1,1-dioxide are heated to boiling in 25 ml of abs. xylene for 5 hours. The product which has precipitated after cooling is filtered off, recrystallized from toluene/active charcoal and digested three times with a little ice-cold diethyl ether.

Yield: 0.58 g of yellow crystals (70% of theory)

TLC: solvent Bz:Dx:AcOH=10:1:1; 0.8

M.p.: 194°–195° C. (toluene)

$^1$H-NMR: (DMSO-d$_6$) δ(ppm): 7.99–7.7 (m, 5H, FuH5, TT-H7, BT-H5,6,7); 7.69–7.52 (m, 2H, BT-H4, BT-H3); 7.42–7.31 (m, 2H, Py-H3,4); 7.27 (d, 1H, Fu-H3) 6.75–6.68 (m, 2H, Fu-H3, Py-H5); 5.75 (S, 2H, OC$\underline{H}_2$); 3.05 (s, 3H, —C$\underline{H}_3$)

$^{13}$C-NMR: (DMSO-d$_6$) δ(ppm): 166.0; 161.2; 155.0; 148.1; 146.7; 144.7; 141.3; 140.2; 139.6; 139.4; 138.9; 132.2; 124.6; 124.4; 124.2; 123.7; 122.4; 117.9; 113.0; 110.5; 108.2; 109.9; 106.6; 64.9; 62.5; 39.6

The amino component can be prepared as follows:

6-[(2-Benzo[b]thienyl)-methoxy]-2-bromopyridine 8.75 ml (42.7 mmol) of a 30% strength solution of sodium methanolate in abs. methanol are added to 7.01 g (42.7 mmol) of 2-benzo[b]thiophenemethanol in 50 ml of abs. methanol, and the solvent is stripped off at room temperature. The residue is stirred together with 10.11 g (42.2 mmol) of 2,6-dibromopyridine in 250 ml of abs. dimethylformamide at 70°–80° C. for 3 hours. After the solvent has been stripped off, the residue is taken up in ethyl acetate, washed with 0.5N hydrochloric acid, dried over sodium sulphate and filtered, and the solvent is stripped off. The crude product is recrystallized from diethyl ether/active charcoal.

Yield: 10.37 g of colourless crystals (75% of theory)

TLC: solvent PE:Bz=4:1; 0.35

M.p.: 82°–83° C. (diethyl ether)

$^1$H-NMR (CDCl$_3$): δ(ppm): 7.88–7.71 (m, 2H, BT-H4,7); 7.40 (dd, 1H, Py-H4); 7.39–7.28 (m, 3H, BT-H3,5,6); 7.11 (d, 1H, Py-H3); 6.76 (d, 1H, Py-H5); 5.63 (s, 2H, —OC$\underline{H}_2$)

$^{13}$C-NMR (CDCl$_3$): δ(ppm): 162.4; 140.6; 140.4; 139.5; 139.2; 138.3; 124.5; 124.2; 124.2; 123.7; 122.3; 120.8; 109.7; 63.5

6[(2Benzo[b]thienyl-methoxy]-2-pyridamine 7.96 ml (19.89 mmol) of a 2.5N solution of butyllithium in n-hexane are added to 6.37 g (19.89 mmol) of 6-[(2-benzo[b]thienyl)methoxy]-2-bromopyridine in 70 ml of abs. tetrahydrofuran at −80° C., and the mixture is stirred for 30 minutes. Then, at −80° C., 2.88 g (19.89 mmol) of 1-azido-1-phenylethene in 28 ml of abs. tetrahydrofuran are added. After room temperature has been reached, 300 ml of 10% strength hydrochloric acid are added, and the mixture is stirred for 20 minutes and adjusted to pH=12 with sodium hydroxide pellets. The aqueous phase is extracted 9 times with 30 ml of ethyl acetate each time. The combined organic phases are dried over sodium sulphate and filtered, and the solvent is stripped off. The product is isolated by column chromatography. (Mobile phase: chloroform; 210 g of silica gel).

Yield: 1.49 g of colourless crystals (30% of theory)

TLC: solvent CHCl$_3$; 0.1

M.p.: 91°–94° C.

$^1$H-NMR (CDCl$_3$): δ(ppm): 7.86–7.69 (m, 2H, BT-H4,7); 7.39 (dd, 1H, Py-H4); 7.33–7.28 (m, 3H, BT-H3,5,6); 6.28 (d, 1H, Py-H3); 6.10 (d, 1H, Py-H5); 5.56 (s, 2H, —OC$\underline{H}_2$)

$^{13}$C-NMR: (CDCl$_3$): δ(ppm): 162.2; 156.9; 140.9; 140.4; 140.3; 139.2; 124.1; 124.1; 123.4; 123.2; 122.3; 100.1; 99.1; 62.4

EXAMPLE 23

6-(2-Benzo[b]furanyl)-4-hydroxy-2methyl-N-(6-phenyl-2-pyridinyl)-2H-thieno[2,3-e]-1,2-thiazine-3-carboxamide 1,1-dioxide 0.20 g (0.51 mmol) of methyl 6-(2-benzo[b]furanyl)-4-hydroxy-2-methyl-2H-thieno[2,3-e]-1,2-thiazine-3-carboxylate 1,1-dioxide and 0.09 g (0.51 mmol) of 6-phenyl-2-pyridinamine are heated to boiling in 2 ml of absolute xylene for 7 hours. The cooled reaction mixture is filtered and digested with 5 ml of cold diethyl ether. The crude product is recrystallized from dimethyl sulphoxide/active charcoal.

Yield: 70 mg of yellow crystals (25.8% of theory)

TLC: solvent PE:EtOH=3:1; 0.3

M.p.: decompostion above 225° C. (DMSO)

$^1$H-NMR: (DMSO-d$_6$) d(ppm): 8.16–8.08 (m, 3H, Bzfu-H3, Py-H3,5); 8.06–7.89 (m, 2H, Bzfu-H4,7); 7.84–7.63 (m, 4H, Bz-H3,4,5, Py-H4); 7.58–7.47 (3H, Bz-H2,6, Thaz-H7); 7.47–7.28 (m, 2H, Bzfu-H5,6); 3.02 (s, 3H, OCH$_3$)

The starting material can be prepared as follows:

2-Cyano-1-(2-benzo[b]furyl)ethenyl 4-methylbenzenesulphonate 27.18 g (142.56 mmol) of p-toluenensulphonyl chloride in 50 ml of absolute dichloromethane are added dropwise to 24.00 g (129.60 mmol) of b-oxo-2-benzo[b]furanpropanenitrile and 14.42 g (142.56 mmol) of N-methylmorpholine in 180 ml of absolute dichloromethane at room temperature, and the mixture is stirred for one hour. The reaction mixture is washed with 2×100 ml of water and once with 50 ml of 2N hydrochloric acid. The organic phase is dried over Na$_2$SO$_4$/active charcoal and filtered, and the the solvent is distilled off. The resulting solid is digested with cold diisopropyl ether.

Yield: 35.92 g of colourless crystals (81.7% of theory)

TLC: solvent PE:EA=5:1; 0.4

M.p.: 143°–145° C. (DIPE)

$^1$H-NMR: (CDCl$_3$) d(ppm): 8.03 (d, 2H, Bz-H2,6); 7.65 (d, 1H, Bzfu-H4) 7.55–7.24 (m, 6H, Bz-H3,5, Bzfu-H3,5,6,7); 5.91 (s, 1H, =CH); 2.50 (s, 3H, C$\underline{H}_3$)

$^{13}$C-NMR: (DMSO-d$_6$) d(ppm): 155.1; 150.3; 147.0; 146.8; 130.9; 130.4; 128.5; 127.9; 127.1; 124.2; 122.8; 114.1; 111.9; 111.5; 90.6; 21.1

Methyl 3-amino-5-(2-benzo[b]furanyl)-2-thiophenecarboxylate 11.63 g (109.53 mmol) of methyl thioglycolate are added to 19.67 g (109.53 mmol) of 30% strength sodium methanolate in 350 ml of absolute methanol at 15°–20° C., and the mixture is stirred at room temperature for 20 minutes. Subsequently 35.4 g (104.31 mmol) of 2-cyano-1-(2-benzo[b]furanyl)ethenyl 4-methylbenzenesulphonate are added in one portion, and the mixture is stirred for a further 1½ hours.

After the solvent has been stripped off, the residue is partitioned between 300 ml of water and 200 ml of dichloromethane, extraction is carried out three times more with 100 ml of dichloromethane, and the organic phase is dried over Na$_2$SO$_4$/active charcoal and filtered, and the solvent is stripped off. The crude product is recrystallized from ethanol/active charcoal.

Yield: 17.10 g of colourless crystals (60.0% of theory)

TLC (amine): solvent PE:EA=2:1; 0.60

M.p.: 160°–162° C. (ethanol)

$^1$H-NMR: (DMSO-d$_6$) d(ppm): 7.70–7.59 (m, 2H, Bzfu-H4,7); 7.42–7.24 (m, 3H, Bzfu-H3,5,6); 7.10 (s, 1H, Th-H4); 3.37 (s, 3H, OCH$_3$)

$^{13}$C-NMR: (DMSO-d$_6$) d(ppm): 163.9; 155.0; 154.2; 147.7; 135.9; 128.3; 125.5; 123.6; 121.5; 116.9; 111.1; 104.0; 97.4; 51.1

Methyl 5-(benzo[b]furanyl)-3-chlorosulphonyl-2-thiophenecarboxylate 15.76 g (57.69 mmol) of methyl 3-amino-5-(2-benzo[b]furanyl)-2-thiophenecarboxylate in 50 ml of abs. diethyl ether are stirred with 41.20 g of 11.5% strength ethereal hydrochloric acid for 10 minutes, and the solvent is stripped off. 4.18 g (60.53 mmol) of sodium nitrite in 8 ml of water are introduced under the surface of the liquid into a suspension of 16.80 g (54.23 mmol) of this hydrochloride in 100 ml of concentrated hydrochloric acid at 0° C. over the course of 1 hour, and the mixture is stirred for two hours. This solution is poured into a mixture of 450 ml of saturated sulphurdioxide solution in glacial acetic acid (~40% strength) and 29 ml of a saturated aqueous copper(II) chloride solution, heated to 30° C. and stirred for 1 hour. The reaction mixture is poured into 600 l of ice-water and extracted with 4×100 ml of dichloromethane, and the combined organic phases are washed with 2×100 ml of water. The organic phase is dried over $Na=SO_4$/active charcoal and filtered, the solvent is stripped off, and the crude product is digested with cold diethyl ether.

Yield: 12.60 g of yellow crystals (65.5% of theory)

TLC: solvent PE:EtOH=2:1; 0.8

M.p.: 158°–160° C. (ether)

$^1$H-NMR: (CDCl$_3$) d(ppm): 7.90 (s, 1H, Th-H4); 7.63 (d, 1H, Bzfu-H4); 7.53 (d, 1H, Bzfu-H7); 7.44–7.25 (m, 2H, Bzfu-H5,6); 7.12 (s, 1H, Bzfu-H3)

$_{13}$C-NMR: (CDCl$_3$) d(ppm): 161.2; 154.8; 153.0; 149.7; 134.4; 129.0; 128.3; 128.25; 126.1; 124.3; 122.2; 111.7; 104.7; 53.1

Methyl 5-(2-benzo[b]furyl)-3-[N-methoxycarbonylmethyl)sulphamoyl]-2-thiophenecarboxylate A suspension of 11.6 g (32.51 mmol) of methyl 5-(2-benzo[b]furanyl)-3-chlorosulphonyl-2-thiophenecarboxylate, 5.94 g (43 mmol) of potassium carbonate and 5.4 g (43 mmol) of glycine methyl ester hydrochloride in 60 ml of abs. dichloromethane and 18 ml of absolute methanol is heated to boiling for 6 hours. The reaction mixture is poured into 300 ml of ice-cold 2N hydrochloric acid, and the resulting crystals are filtered off and digested three times with 50 ml of ice-cold water each time. The crude product is recrystallized from methanol/active charcoal.

Yield: 10.97 g of yellow crystals (76% of theory)

TLC: solvent PE:EA=2:1; 0.45

M.p.: 156°–158° C. (methanol)

$^1$H-NMR: (CDCl$_3$) d(ppm): 7.96–7.83 (m, 2H, NH, Th-H4); 7.75–7.60 (m, 3H, Bzfu-3,4,7); 7.46–7.25 (m, 2H, Bzfu-H5,6); 3.97 (d, 2H, CH$_2$); 3.88 (s, 3H, Th-COOCH$_3$); 3.55 (s, 3H, CH$_2$COOCH$_3$)

Methyl 6-(2-benzo[b]furanyl)-4-hydroxy-2H-thieno[2,3-e]-1,2-thiazine-3-carboxylate 1,1-dioxide 3.6 g (8.79 mmol) of methyl 5-(2-benzo[b]-furanyl)-3-[N-(methoxycarbonylmethyl) sulphamoyl]-2-thiophenecarboxylate in 36 ml of absolute tetrahydrofuran are added dropwise to 2.17 g (19.34 mmol) of potassium tertbutanolate in 26 ml of absolute tetrahydrofuran at −10° to −5° C., and the mixture is stirred for 1 hour. After addition of 159 ml of ice-cold 2N hydrochloric acid, the crude product is extracted with 6×100 ml, the solvent is distilled off, and the residue is evaporated 2× with 100 ml of benzene. This crude product is digested with a little cold acetonitrile.

Yield: 1.60 g of yellow crystals (48.2% of theory)

TLC: solvent Bz:MeOH=3:1; 0.6

M.p.: decomposition above 235° C. (methanol)

$^1$H-NMR: (DMSO-d$_6$) d(ppm): 8.12 (s, 1H, Thaz-H7); 7.75–7.60 (m, 3H, Bzfu-H3,4,7); 7.45–7.24 (m, 2H, Bzfu-H5,6); 3.90 (s, 3H, OCH$_3$)

Methyl 6-(2-benzo[b]furanyl)-4-hydroxy-2-methyl-2H-thieno[2,3-e]-1,2-thiazine-3-carboxylate 1,1-dioxide 700 mg (1.85 mmol) of methyl 6-(2-benzo[b]furanyl)-4-hydroxy-2H-thieno[2,3-e]-1,2-thiazine-3-carboxylate 1,1-dioxide in 2.4 ml of absolute DMF are added dropwise to a suspension of 49 mg (2.04 mmol) of sodium hydride in 1.2 ml of absolute DMF at 7° C., and the mixture is stirred for one hour. 0.32 g (2.23 mmol) of iodomethane is added to the resulting solution, and the mixture is stirred at room temperature for 20 hours. After addition of 20 ml of ice-cold 2N-hydrochloric acid, the crude product is extracted with 4×20 ml of dichloromethane, the combined organic phases are dried and filtered, and the solvent is stripped off. This is digested with 2×20 ml of hot ethanol.

Yield: 0.35 g of yellow crystals (48.2% of theory)

TLC: solvent Bz:MeOH=3:1; 0.8

M.p.: decomposition above 220° C. (crude)

$^1$H-NMR: (DMSO-d$_6$) d(ppm): 8.22 (s, 1H, Thaz-H7); 7.79–7.62 (m, 3H, Bzfu-H3,4,7); 7.48–7.27 (m, 2H, Bzfu-H5,6); 3.90 (s, 3H, OCH$_3$); 3.02 (s, 3H, NCH$_3$)

EXAMPLE 14

The formation of prostaglandin D$_2$ by neutrophils was used as a measure of the cyclooxygenase activity, and the formation of leucotrien B$_4$ as a measure of the 5-lipoxygenase activity.

Male Sprague-Dawley rats (250–300 g) received 1 mg of lambda-carageenan (dissolved in 0.5 ml of distilled water) injected intraperitoneally.

After 16 hours, the rats were sacrificed by exposure to diethyl ether. 15 ml of Hanks balanced salt solution (HBSS) were injected i.p., the neutrophils were harvested by aspiration (10 ml) and were centrifuged (5 min, 100 g, 4° C.), the supernatant solution was decanted, and the cells were resuspended in HBSS at 4° C. to a concentration of 5×10$^6$ cells/ml.

400 μl of cell suspension (2×10$^6$ cells), 0.5 μg of compound dissolved in DMSO and 49.5 μl of HBSS were incubated at 37° C. for 5 min. Then 50 μl of A23187 (2 μmol/l final concentration) were added and subsequently the mixture was again incubated at 37° C. for 5 min.

The reaction was stopped by centrifugation at 10,000 g for 3 s, and the supernatant liquid was transferred into precooled plastic tubes and left in an ice bath for a maximum of 1 h before starting the radioimmunoassay measurement.

PGD$_2$ and LTB$_4$ were measured after dilution with HBSS using commercial RIA kits.

The comparison substance was 6-chloro-2-methyl-N-(2-pyridyl)-2H-thieno[2,3-e]-1,2-thiazine-3-carboxamide 1,1-dioxide ("LORNOXICAM", Compound A).

| Compound | IC$_{50}$ (μmol/l) | |
|---|---|---|
| | PGD$_2$ | LTB$_4$ |
| A | 0.02 | >10 |
| 1 | 0.017 | >10 |
| 2 | 0.027 | >10 |
| 3 | 0.017 | 5.2 |
| 4 | 3.4 | 0.47 |
| 5 | 0.27 | 0.66 |
| 6 | 3.6 | 0.58 |
| 7 | 1.6 | 0.73 |
| 8 | 0.1 | 2.2 |
| 9 | 0.039 | 1.6 |
| 11 | 0.2 | 2.1 |
| 12 | 0.19 | 2.7 |
| 14 | 0.038 | >10 |
| 15 | 0.0035 | >10 |
| 16 | 0.0096 | >10 |
| 17 | 0.19 | 1.3 |
| 18 | 0.068 | 1.3 |
| 19 | 0.039 | 1.4 |

What we claim is:

1. A compound of the formula

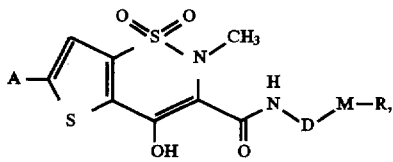
(I)

in which:

A is lower alkyl, halogen, nitro, cyano, phenyl,

or

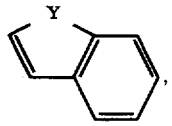

where
Y is O or S;

D is 2-pyridyl or

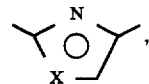

where
X is CH, RN$^6$, O or S with R$^6$ being hydrogen or lower alkyl;

M is a single bond, a straight or branched carbon chain with 1 to 12 carbon atoms in the chain, said chain containing one or more double and/or triple bonds and/or one of the heteroatoms N, O and S, or is

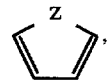

where
Z is N, O or S;
R is hydrogen or —R$^1{}_n$—R$^2$, where
R$^2$ is phenyl, halogenated phenyl, or

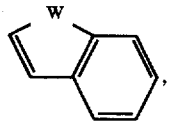

where
R$^1$ and W independently are O or S and
n is 0 or 1;
under the proviso that —M—R is not hydrogen or lower alkyl when D denotes 2-pyridyl, oxazolyl or thiazolyl and A is halogen;
and their pharmaceutically acceptable salts.

2. The compound according to claim 1, in which M is a single bond, methoxy or furyl.

3. The compound according to claim 1, in which D is pyridyl, thiazolyl or oxazolyl.

4. The compound according to claim 3, in which D is 2-pyridyl and the substituents —M—R are linked at position 6 on the pyridine nucleus.

5. The compound according to claim 1, in which A is chlorine, furyl, thienyl, phenyl or benzo[b]furyl.

6. The compound according to claim 4, in which R is hydrogen, fluorinated phenyl, fluorinated phenoxyl, benzo[b]furyl or benzo[b]thienyl.

7. A pharmaceutical composition for the treatment of inflammation and pain, which comprises the compound of claim 1 and a pharmaceutically acceptable carrier.

8. A method for the treatment of inflammation and pain which comprises administering to a subject in need thereof, an effective amount of a compound of claim 1.

* * * * *